United States Patent [19]

Mills et al.

[11] Patent Number: 5,344,830
[45] Date of Patent: Sep. 6, 1994

[54] N,N-DIACYLPIPERAZINE TACHYKININ ANTAGONISTS

[75] Inventors: Sander G. Mills, Woodbridge; Richard J. Budhu, Monmouth Junction; Conrad P. Dorn, Plainfield; William J. Greenlee, Teaneck; Malcolm MacCoss, Freehold; Mu T. Wu, Clark, all of N.J.

[73] Assignee: Merck & Co., Inc., Rahway, N.J.

[21] Appl. No.: 988,514

[22] Filed: Dec. 10, 1992

[51] Int. Cl.[5] .................. A61K 31/495; C07D 241/04; C07D 401/12; C07D 413/12
[52] U.S. Cl. .............................. 514/235.8; 514/227.8; 514/228.2; 514/232.5; 514/253; 514/255; 514/252; 544/60; 544/121; 544/357; 544/360; 544/361; 544/372; 544/387; 544/388; 544/336; 544/390; 558/390; 560/25; 560/157
[58] Field of Search ................. 544/387, 388, 360, 60, 544/121, 357, 372, 361; 514/227.8, 228.2, 232.5, 235.8, 252, 253, 255

[56] References Cited

U.S. PATENT DOCUMENTS

| | | | |
|---|---|---|---|
| 3,288,795 | 11/1966 | Irikura et al. | 544/387 |
| 4,804,661 | 2/1989 | Ferrini et al. | 514/255 |
| 4,923,870 | 5/1990 | Braquest et al. | 435/255 |
| 4,943,578 | 7/1990 | Naylor et al. | 514/252 |
| 5,019,576 | 11/1991 | Braquest et al. | 514/255 |
| 5,064,838 | 11/1991 | Carr et al. | 514/317 |

FOREIGN PATENT DOCUMENTS

| | | |
|---|---|---|
| 0343900 | 11/1989 | |
| 0368670 | 5/1990 | |
| 0436334 | 7/1991 | European Pat. Off. |
| 0499313 | 8/1992 | European Pat. Off. |
| WO90/05525 | 5/1990 | |
| WO90/05729 | 5/1990 | PCT Int'l Appl. |
| WO91/18899 | 12/1991 | PCT Int'l Appl. |
| WO92/01679 | 2/1992 | PCT Int'l Appl. |
| WO92/06079 | 4/1992 | PCT Int'l Appl. |
| WO92/12128 | 7/1992 | PCT Int'l Appl. |
| WO92/20661 | 11/1992 | PCT Int'l Appl. |
| WO92/21677 | 12/1992 | PCT Int'l Appl. |

OTHER PUBLICATIONS

Rivett et al *Australian J. Chem.*, 19, 165 (1966).
*Pol. J. Pharmacol. Pharm.*, 38, 545 (1986), Korzycka et al.
*Bull. Chem. Soc. Japan*, 60(9), 3450–3452 (1987), Soai, et al.
*Tetrahedron Lett.*, 30, 5193 (1989), Bigge, et al.
*Bioorg. & Med. Chem. Lett.*, 2(10), 1275–1278 (1992), Birch, et al.
*Life Sci.*, 50, PL-101-PL-106 (1992), Emonds-Alt et al.

Primary Examiner—Emily Bernhardt
Attorney, Agent, or Firm—Joseph F. DiPrima; David L. Rose; J. Eric Thies

[57] ABSTRACT

Diacylpiperazines of general structure

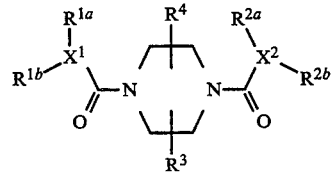

are tachykinin receptor antagonists useful in the treatment of inflammatory diseases, pain or migraine, and asthma, and calcium channel blockers useful in the treatment of cardiovascular conditions such as angina, hypertension or ischemia.

4 Claims, No Drawings

N,N-DIACYLPIPERAZINE TACHYKININ ANTAGONISTS

SUMMARY OF THE INVENTION

This invention is concerned with novel compounds represented by structural formula I:

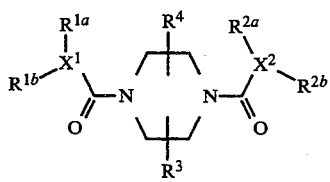

wherein $X^1$, $X^2$, $R^{1a}$, $R^{1b}$, $R^{2a}$, $R^{2b}$, $R^3$ and $R^4$ are hereinafter defined.

The invention is also concerned with pharmaceutical formulations with these novel compounds as active ingredients and the use of the novel compounds and their formulations in the treatment of certain disorders.

The compounds of this invention have activity as tachykinin receptor antagonists and are useful in the treatment of inflammatory diseases and pain or migraine.

Also, some of these compounds are calcium channel blockers and are useful in the treatment of cardiovascular disorders such as angina, hypertension or ischemia.

Also, these compounds may be angiotensin II (A-II) antagonists selective for the type 2 ($AT_2$) subtype useful in the treatment of cerebrovascular, cognitive, and CNS disorders.

BACKGROUND OF THE INVENTION

Analgesia has historically been achieved in the central nervous system by opiates and analogs which are addictive, and peripherally by cyclooxygenase inhibitors that have gastric side effects. Substance P antagonists induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85-141>. The NK1 and NK2 receptor subtypes are implicated in synaptic transmission (Laneuville et al., *Life Sci.* 42:1295-1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene mas, the yeast mating factor receptors, a Dictyostelium cAMP receptor, and receptors for other hormones and neurotransmitters (see A. D. Hershey, et al., *J. Biol. Chem.*, 1991, 226, 4366-4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nonmenclature designates the receptors for SP, neurokinin A, and neurokinin B as NK-1, NK-2, and NK-3, respectively.

More specifically, substance P is a pharmacologically-active neuropeptide that is produced in mammals and possesses a characteristic amino acid sequence that is illustrated below:

Arg-Pro-Lys-Pro-Gln-Gln-Phe-Phe-Gly-Leu-Met-$NH_2$ (Chang etal., *Nature New Biol.* 232, 86 (1971); D. F. Veber etal., U.S. Pat. No. 4,680,283).

Neurokinin A possesses the following amino acid sequence:
His-Lys-Thr-Asp-Ser-Phe-Val-Gly-Leu-Met-$NH_2$.

Neurokinin B possesses the following amino acid sequence:
Asp-Met-His-Asp-Phe-Phe-Val-Gly-Leu-Met-$NH_2$.

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, 199, 1359 (1978); P. Oehme et al., *Science*, 208, 305 (1980)) and plays a role in sensory transmission and pain perception (T. M. Jessell, *Advan. Biochem. Psychopharmacol.* 28, 189 (1981)). For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13-34 <published by Pitman) and Otsuka and Yanagisawa, "Does Substance P Act as a Pain Transmitter?" TIPS (December 1987) 8 506-510]. In particular, substance P has been shown to be involved in the transmission of pain in migraine (see B. E. B. Sandberg et al., *Journal of Medicinal Chemistry*, 25, 1009 (1982)), and in arthritis (Levine et al. *Science*, (1984) 226 547-549). These peptides have also been implicated in gastrointestinal (GI) disorders and diseases of the GI tract, such as inflammatory bowel disease, ulcerative colitis and Crohn's disease, etc. (see Mantyh et al., *Neuroscience*, 25 (3), 817-37 (1988) and D. Regoli in "Trends in Cluster Headache" Ed. F. Sicuteri et al., Elsevier Scientific Publishers, Amsterdam, 1987, pp. 85-95).

It is also hypothesized that there is a neurogenic mechanism for arthritis in which substance P may play a role (Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in *J. Rheumatol.* (1988) 15(12) 1807-10). Therefore, substance P is believed to be involved in the inflammatory response in diseases such as rheumatoid arthritis and osteoarthritis (O'Byrne et al., in Arthritis and Rheumatism (1990) 33 1023-8). Other disease areas where tachykinin antagonists are believed to be useful are allergic conditions (Hamelet et al., Can. J. Pharmacol.

Physiol. (1988) 66 1361–7), immunoregulation (Lotz et al., Science (1988) 241 1218–21, Kimball et al., J. Immunol. (1988) 141 (10) 3564–9 and A. Perianin, et al., *Biochem. Biophys, Res. Commun.* 161, 520 (1989)) vasodilation, bronchospasm, reflex or neuronal control of the viscera (Mantyh et al., PNAS (1988) 85 3235–9) and, possibly by arresting or slowing β-amyloid-mediated neurodegenerative changes (Yankner et al., *Science*, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th June–2nd July, 1992, in press]. Antagonists selective for the substance P and-/or the neurokinin A receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992)).

In the recent past, some attempts have been made to provide peptide-like substances that are antagonists for substance P and other tachykinin peptides in order to more effectively treat the various disorders and diseases listed above. See for example European patent applications (EPO Publication Nos. 0,347,802, 0,401,177 and 0,412,452) which disclose various peptides as neurokinin A antagonists. Similarly, *EPO Publication No.* 0,336,230 discloses heptapeptides which are substance P antagonists useful in the treatment of asthma. Merck U.S. Pat. No. 4,680,283 also discloses peptidal analogs of substance P.

Certain inhibitors of tachykinins have been described in U.S. Pat. No. 4,501,733, by replacing residues in substance P sequence by Trp residues.

A further class of tachykinin receptor antagonists, comprising a monomeric or dimeric hexa- or heptapeptide unit in linear or cyclic form, is described in GB-A-2216529.

The peptide-like nature of such substances makes them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known in the art that baclofen (S-(aminoethyl)-4-chlorobenzenepropanoic acid) in the central nervous system effectively blocks the excitatory activity of substance P, but because in many areas the excitatory responses to other compounds such as acetylcholine and glutamate are inhibited as well, baclofen is not considered a specific substance P antagonist. Pfizer WIPO patent applications (PCT Publication Nos. WO 90/05525, WO 90/05729, WO 91/18899, WO 92/12151 and WO 92/12152) and publications (*Science*, 251, 435–437 (1991); *Science*, 251, 437–439 (1991); *J. Med Chem.*, 35, 2591–2600 (1992)) disclose 2-arylmethyl-3-substituted amino-quinuclidine derivatives which are which are disclosed as being useful as substance P antagonists for treating gastrointestinal disorders, central nervous system disorders, inflammatory diseases and pain or migraine. A Glaxo European patent application (*EPO Publication No.* 0,360,390) discloses various spirolactam-substituted amino acids and peptides which are antagonists or agonists of substance P. A Pfizer European patent application (*EPO Publication No.* 0,436,334) discloses certain 3-aminopiperidive derivatives as substance P antagonists. A Pfizer WIPO patent application (*PCT Publication No. WO* 92/06079) discloses fused-ring analogs of nitrogen-containing nonaromatic heterocycles as useful for the treatment of diseases mediated by an excess of substance P. A Sanofi publication (*Life Sci.*, 50, PL101–PL106 (1992)) discloses a 4-phenyl piperidine derivative as an antagonist of the neurokinin A (NK2) receptor. A Du Pont Merck WIPO patent application (*PCT Publication No. WO* 92/12128) discloses certain piperidine and pyrrolidine compounds as analgesic agents. A Pfizer WIPO patent application (*PCT Publication No. WO* 92/15585) discloses 1-azabicyclo-[3.2.2]-nonan-3-amine derivatives as substance P antagonists. U.S. Pat. Nos. 4,804,661 and 4,943,578 disclose certain piperazine compounds as analgesics. U.S. Pat. No. 5,064,838 discloses certain 1,4-disubstituted piperidinyl compounds as analgesics. *EPO Publication* 0,499,313 discloses certain 3-oxy and 3-thio azabicyclic compounds as central nervous system stimulants. *PCT Publication No. WO* 92/01679 discloses certain 1,4-disubstituted piperazines useful in the treatment of mental disorders in which a dopaminergic deficit is implicated. Certain phenylacetylpiperazines have been disclosed as peripherally selective kappa-opioid receptor antagonists (Birch, et. al., *Bioorg. & Med. Chem. Lett.*, 2(10), 1275–1278(1992)).

Calcium channel blocking agents are a known group of drugs which act to inhibit transfer of calcium ions across the plasma membrane of cells. It is known that the influx of calcium ions into certain cells in the mammalian body, including the vascular smooth muscle cells and myocardial cells, participates in the activity of such cells and that the administration of calcium channel blockers (also known as calcium antagonists or calcium entry blockers), which inhibit such influx, would suppress myocardial contractile force and rate and cause vasodilation. Calcium channel blockers delay or prevent the cardiac contracture which is believed to be caused by an accumulation of intracellular calcium under ischemic conditions. Calcium overload, during ischemia, can have a number of additional adverse effects which would further compromise the ischemic myocardium. These include less efficient use of oxygen for ATP production, activation of mitochondrial fatty acid oxidation, and possibly, promotion of cell necrosis. Calcium channel blockers are, therefore, useful in the treatment or prevention of a variety of diseases and disorders of the heart and vascular system, such as angina pectoris, myocardial infarction, cardiac arrhythmia, cardiac hypertrophy, coronary vasospasm, hypertension, cerebrovascular spasm and other ischemic disease. In addition, certain calcium channel blocking agents are capable of lowering elevated intraocular pressure when administered topically to the hypertensive eye in solution in a suitable ophthalmic vehicle.

Also, certain calcium channel blockers sensitize multidrug resistant cells to certain chemotherapeutic agents and are useful in the reversal of multidrug resistance by enhancing the efficacy of various anticancer agents (*J. Biol Chem.*, 262 (5), 2166–2170 (1987); *Scientific American*, 44–51 (March 1989)). In addition, certain calcium channel blockers are suggested as having activity in blocking calcium channels in insect brain membranes and so are useful as insecticides (*EMBO J.*, 8(8), 2365–2371 (1989)).

A number of compounds having calcium channel blocking activity are known, for example certain dihydropyridine derivatives, such as nifedipine and nicardipine, and other compounds such as verapamil, diltiazem and flunarizine.

Some compounds of chemical structures somewhat similar to those of the compounds of the present invention have been reported in U.S. Pat. Nos. 4,089,958 and 4,138,564. However, they are reported as chemical intermediates only.

Some 1,4-bis(diphenylacetyl)piperazines (without substituents on the piperazine ring carbons) have been disclosed as analgesic, antipyretic, and antiinflammatory agents and CNS depressants (U.S. Pat. No. 3,288,795). The preparation of 1,4-bis(diphenylcarbamoyl)piperazine has been reported [D. E. Rivett and J. F. K. Wilshire, *Australian J. Chem.*, 19, 165 (1966)]. Unsymmetrical 1-acyl-4-(diphenylcarbamoyl)piperazines and 1-acyl-4-(dialkylcarbamoyl)piperazines have also been described [L. Korzycka, et al., *Pol. J. Pharmacol. Pharm.*, 38, 545 (1986); L. Toldy, et al *Acta Chim. Acad. Sci. Hung.*, 70, 101 (1971)]. All of these are unsubstituted on the piperazine ring carbons.

Certain 1,4-diacylpiperazine-2-carboxylates and related derivatives in which at least one of the acyl groups is substituted benzoyl have been disclosed as platelet-activating factor antagonists (U.S. Pat. No. 4,923,870 and European Patent Publication 0,368,670). Methyl 4-(benzyloxycarbonyl)-1-(tert-butoxycarbonyl)piperazine-2-carboxylate has been reported as an intermediate (EP 0,368,670), as has methyl 1-(benzyloxycarbonyl)-4-tert)-butoxycarbonyl)piperazine-2-carboxylate and the coresponding acid [C. F. Bigge, et al., *Tetrahedron Lett.*, 30, 5193 (1989).

DETAILED DESCRIPTION OF THE INVENTION

The novel compounds of this invention are represented by structural formula I:

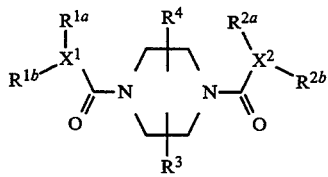

or a pharmaceutically acceptable salt thereof, wherein:
$R^{1a}$ is selected from the group consisting of:
1) H,
2) $C_{1-8}$ alkyl,
3) phenyl, either unsubstituted or substituted with one or two substituents selected from the group consisting of:
 a) —$C_{1-4}$ alkyl,
 b) —halo,
 c) —OH,
 d) —$CF_3$,
 e) —$NH_2$,
 f) —NH($C_{1-4}$ alkyl),
 g) —N($C_{1-4}$ alkyl)($C_{1-4}$ alkyl),
 h) —$CO_2H$,
 i) —$CO_2$($C_{1-4}$ alkyl), and
 j) —$C_{1-4}$ alkoxy;
4) —$C_{1-4}$ alkyl-phenyl, wherein the phenyl is either unsubstituted or substituted with one or two substituents selected from:
 a) —$C_{1-4}$ alkyl,
 b) —halo,
 e) —OH,
 d) —$CF_3$
 e) —$NH_2$,
 f) —NH($C_{1-4}$ alkyl),
 g) —N($C_{1-4}$ alkyl)$_2$,
 h) —$CO_2H$,
 i) —$CO_2$($C_{1-4}$ alkyl), and
 j) —$C_{1-4}$ alkoxy;

$R^{1b}$ is selected from the group consisting of:
1) $R^{1a}$
2) —$C_{3-7}$ cycloalkyl, and
3) —$CH_2$—$R^{1a}$;

$R^{2a}$ and $R^{2b}$ are independently phenyl, either unsubstituted or substituted with one or two substitutents selected from the group consisting of:
1) —$C_{1-4}$ alkoxy,
2) —halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
 a) —halo,
 b) —OH,
 c) —$CF_3$,
 d) —$NH_2$,
 e) —NH($C_{1-4}$ alkyl),
 f) —N($C_{1-4}$ alkyl)($C_{1-4}$ alkyl)
 g) —$CO_2H$,
 h) —$CO_2$($C_{1-4}$ alkyl),
 i) $C_{1-4}$alkoxy,
 j) —S(O)$_x$($C_{1-4}$ alkyl) wherein x is 0, 1 or 2,
 k) —$C_{3-7}$ cycloalkyl;

and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;
$X^1$ is —N, —CH or O, and if $X^1$ is O, $R^{1a}$ is absent;
$X^2$ is —N or —CH;
$R^3$ is selected from the group consisting of:
1) —$CONR^7R^8$,
2) —$CO_2R^9$,
3) —$CON(R^6)CONR^5R^6$,
4) $C_{2-6}$ alkyl substituted with one or more substituents selected from the group consisting of:
 a) —OH,
 b) —$OR^5$,
 c) —$OCOR^6$,
 d) —$S(O)_xR^5$,
 e) —$OCONR^5R^6$,
 f) —$CONR^5R^6$,
 g) —$CO_2R^6$,
 h) —$N(R^6)CONR^5R^6$,
 i) —$NH_2$,
 j) —$NHR^5$,
 k) —$NR^5R^6$,
$R^4$ is H or is independently selected from the definitions of $R^3$;
$R^5$ is $C_{1-6}$ alkyl either unsubstituted or substituted with one or more substituents selected from the group consisting of:
1) —halo,
2) —OH,
3) —$CF_3$, 4) —NH$_2$,
5) —NH(C$_{1-4}$ alkyl),
6) —N(C$_{1-4}$ alkyl)$_2$,
7) —CO$_2$H,
8) —CO$_2$(C$_{1-4}$ alkyl),
9) —C$_{3-7}$ cycloalkyl,
10) phenyl, either unsubstituted or substituted with one or more of the substituents selected from the group consisting of:
   a) —C$_{1-4}$ alkyl,
   b) —halo,
   c) —OH,
   d) —C$_{1-4}$ alkoxy,
   e) —CF$_3$,
   f) —NH$_2$,
   g) —NH(C$_{1-4}$ alkyl),
   h) —N(C$_{1-4}$ alkyl)(C$_{1-4}$ alkyl)
   i) —CO$_2$H,
   j) —CO$_2$(C$_{1-4}$ alkyl);

R$^6$ is —H or is independently selected from the definitions of R$^5$; or

R$^5$ and R$^6$ can be joined together to form with the nitrogen to which they are attached —N(CH$_2$CH$_2$)L, wherein L is selected from:
i) a single bond.
ii) —CH$_2$—,
iii) —O—,
iv) —S(O)$_p$—,
v) —NH—,
vi) —N(R$_7$)—;

R$^7$ is C$_{1-6}$ alkyl substituted with one or more substituents selected from the group consisting of:
1) —NHCO(C$_{1-6}$ alkyl),
2) —N(C$_{1-6}$ alkyl)CO (C$_{1-6}$ alkyl),
3) —NHR$^{10}$,
4) —NR$^{10}$R$^{11}$,
5) —O—C$_{1-6}$ alkyl,
6) —CO$_2$R$^{10}$,
7) 4-morpholinyl,
8) 1-piperidinyl;

R$^8$ is H, C$_{1-6}$ alkyl or is independently selected from the definitions of R$^7$;

R$^9$ is —CH$_2$-phenyl, wherein the phenyl is either unsubstituted or substituted with one or more substituents selected from the group consisting of:
1) —C$_{1-4}$ alkoxy,
2) —halo,
3) —OH,
4) —CF$_3$
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$ alkyl, either unsubstituted or substituted with one or more substituents selected from the group consisting of:
   a) —halo,
   b) —OH,
   c) —CF$_3$,
   d) —NH$_2$,
   e) —NH(C$_{1-4}$ alkyl),
   f) —N(C$_{1-4}$ alkyl)(C$_{1-4}$ alkyl)
   g) —CO$_2$H,
   h) —CO$_2$(C$_{1-4}$ alkyl),
   i) C$_{1-4}$alkoxy,
   j) —S(O)$_x$(C$_{1-4}$ alkyl) wherein x is 0, 1 or 2,
   k) —C$_{3-7}$ cycloalkyl;

R$^{10}$ is —(C$_{1-6}$ alkyl)-phenyl, wherein the phenyl is either unsubstituted or substituted with one or more substituents selected from the group consisting of:
1) —C$_{1-4}$ alkoxy,
2) —halo,
3) —OH,
4) —CF$_3$,
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$alkyl, either unsubstituted or substituted with one or more substituents selected from the group consisting of:
   a) —halo,
   b) —OH,
   c) —CF$_3$,
   d) —NH$_2$,
   e) —NH(C$_{1-4}$ alkyl),
   f) —N(C$_{1-4}$ alkyl)(C$_{1-4}$ alkyl)
   g) —CO$_2$H,
   h) —CO$_2$(C$_{1-4}$ alkyl),
   i) C$_{1-4}$alkoxy,
   j) —S(O)$_x$(C$_{1-4}$ alkyl) wherein x is 0, 1 or 2,
   k) —C$_{3-7}$ cycloalkyl; and R$^{11}$ is C$_{1-6}$ alkyl, or is independently selected from the definitions of R$^{10}$.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, R$^6$, R7, R$^8$, R$^9$, R$^{10}$, R$^{11}$, R$^{12}$, R$^{13}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium.

The term "aryl" means phenyl or naphthyl either unsubstituted or substituted with one, two or three substituents selected from the group consisting of halo, $C_{1-4}$-alkyl, $C_{1-4}$-alkoxy, $NO_2$, $CF_3$, $C_{1-4}$-alkylthio, OH, $-N(R^6)_2$, $-CO_2R^6$, $C_{1-4}$-polyfluoroalkyl, $C_{3-6}$-polyfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, $-C_{1-4}$-alkyl, $-C_{1-4}$-alkoxy, $-CF_3$, halo, $-NO_2$, $-CO_2R^6$, $-N(R^6)_2$ and a fused benzo group.

One embodiment of the novel compounds of this invention is that wherein $X^1$ and $X^2$ are both N of structural formula:

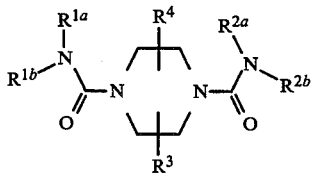

or a pharmaceutically acceptable salt thereof.

A first class of compounds within this embodiment are those compounds wherein:

$R^{1a}$ and $R^{1b}$ are independently H, $C_{1-8}$ alkyl or phenyl, either unsubstituted or substituted with —Cl, —Br, —I, —F, $C_{1-4}$ alkyl, or $C_{1-4}$ alkoxy;

$R^{2a}$ and $R^{2b}$ are independently phenyl, either unsubstituted or substituted with one or two substitutents selected from the group consisting of:
1) —$C_{1-4}$ alkoxy,
2) —halo,
3) —OH,
4) —$CF_3$,
5) —$NH_2$,
6) —$NH(C_{1-4}$ alkyl),
7) —$N(C_{1-4}$ alkyl)$_2$,
8) —$CO_2H$,
9) —$CO_2(C_{1-4}$ alkyl), and
10) —$C_{1-6}$ alkyl, either unsubstituted or substituted with one or more substituents selected from the group consisting of:
  a) —halo,
  b) —OH,
  c) —$CF_3$
  d) —$NH_2$,
  e) —$NH(C_{1-4}$ alkyl),
  f) —$N(C_{1-4}$ alkyl)($C_{1-4}$ alkyl)
  g) —$CO_2H$,
  h) —$CO_2(C_{1-4}$ alkyl),
  i) $C_{1-4}$alkoxy,
  j) —$S(O)_x(C_{1-4}$ alkyl) wherein is 0, 1 or 2,
  k) —$C_{3-7}$ cycloalkyl;
and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;
$R^3$ is —$CONR^7R^8$;
$R^4$ is H or is independently selected from the definitions of $R^3$;

$R^7$ is $C_{1-6}$ alkyl substituted with one or more substituents selected from the group consisting of:
1) —NHCO($C_{1-6}$ alkyl),
2) —N($C_{1-6}$)alkyl)CO($C_{1-6}$ alkyl),
3) —$NHR^{10}$,
4) —$NR^{10}R^{11}$,
5) —O—$C_{1-6}$ alkyl,
6) $CO_2R^{10}$,
7) 4-morpholinyl,
8) 1-piperidinyl;

$R^8$ is H, $C_{1-6}$ alkyl or is independently selected from the definitions of $R^7$;

$R^{10}$ is —($C_{1-6}$ alkyl)-phenyl wherein the phenyl is either unsubstituted or substituted with one or two substitutents selected from the group consisting of:
1) —$C_{1-4}$ alkoxy,
2) —halo,
3) —OH,
4) —$CF_3$,
5) —$NH_2$,
6) —$NH(C_{1-4}$ alkyl),
7) —$N(C_{1-4}$ alkyl)$_2$,
8) —$CO_2H$,
9) —$CO_2(C_{1-4}$ alkyl), and
10) —$C_{1-6}$ alkyl, either unsubstituted or substituted with one or more substituents selected from the group consisting of:
  a) —halo,
  b) —OH,
  c) —$CF_3$,
  d) —$NH_2$,
  e) —$NH(C_{1-4}$ alkyl),
  f) —$N(C_{1-4}$ alkyl)<$C_{1-4}$ alkyl)
  g) —$CO_2H$,
  h) —$CO_2(C_{1-4}$ alkyl),
  i) $C_{1-4}$alkoxy,
  j) $S(O)_x(C_{1-4}$ alkyl) wherein x is 0, 1 or 2,
  k) —$C_{3-7}$ cycloalkyl;

$R^{11}$ is $C_{1-6}$ alkyl, or is independently selected from the definitions of $R^{10}$.

Specific compounds within this first class include:
1) 4-(N,N-di-n-pentylcarbamoyl)-1-(N,N-diphenylcarbamoyl)-N-[3-(4-morpholinyl)propyl]-2-piperazinecarboxamide;
2) 4-(N,N-di-n-pentylcarbamoyl)-1-(N,N-diphenylcarbamoyl)-N-(3-methoxypropyl)-2-piperazinecarboxamide;
3) 4-(N,N-di-n-pentylcarbamoyl)-1-(N,N-diphenylcarbamoyl)-N-[2-(4-morpholinyl)ethyl]-2-piperazinecarboxamide;
4) 4-(N,N-di-n-pentylcarbamoyl)-1-(N,N-diphenylcarbamoyl)-N-[2-(1-piperidinyl)ethyl]-2-piperazinecarboxamide;
5) 4-(N,N-di-n-pentylcarbamoyl)-1-(N,N-diphenylcarbamoyl)-N-[2-(acetamido)ethyl]-2-piperazinecarboxamide;
6) 4-(N,N-di-n-pentylcarbamoyl)-1-(N,N-diphenylcarbamoyl)-N-[2-(N'-benzyl-N'-methylamino)ethyl]-N-methyl-2-piperazinecarboxamide;
7) 4-(N,N-di-n-pentylcarbamoyl)-1-(N,N-diphenylcarbamoyl)-N-[2-(methoxy)ethyl]-2-piperazinecarboxamide;
8) 4-(N,N-di-n-pentylcarbamoyl)-1-(N,N-diphenylcarbamoyl)-N-[3-(benzyloxycarbonyl)propyl]-N-methyl-2-piperazinecarboxamide;
9) 4-(N,N-di-n-pentylcarbamoyl)-1-(N,N-diphenylcarbamoyl)-N-[2-[(N'-(3,5-dimethylphenyl)methyl- (N'-methyl)amino]ethyl]-N-methyl-2-piperazinecarboxamide;

10) 4-(N,N-di-n-pentylcarbamoyl)-1-(N,N-diphenylcarbamoyl)-N-[2-[(N'-[3,5-di-(trifluoromethyl)phenyl]methyl)-(N'-methyl)amino]ethyl]-N-methyl-2-piperazinecarboxamide;

11) 4-(N,N-di-n-pentylcarbamoyl)-1-(N,N-diphenylcarbamoyl)-N-[2-[(N'-(2-methoxyphenyl)methyl)-(N'-methyl)amino]ethyl]-N-methyl-2-piperazinecarboxamide;

13) 4-(N,N-di-n-pentylcarbamoyl)-1-(N,N-diphenylcarbamoyl)-N-[2-(N'-[(1,1-dimethyl)ethoxycarbonyl]-(N'-methyl)aminoethyl]-N-methyl-2-piperazinecarboxamide;

14) (S)-2-(2-(N-(2-methoxybenzyl)amino)ethylaminocarbonyl)-4-(N,N-di-n-pentylcarbamoyl)-1-(N,N-diphenylcarbamoyl)piperazine;

15) 2-(2-(N-methyl-N-(2-methoxybenzyl)amino)ethylaminocarbonyl)-4-(N,N-di-n-pentylcarbamoyl)-1-(N,N-diphenylcarbamoyl)piperazine;

16) (S)-4-(N,N-di-n-pentylcarbamoyl)-1-(N,N-diphenylcarbamoyl)-2-(2-(N-methyl-N-(2-methoxybenzyl)amino)-N-(methyl)ethylaminocarbonyl)piperazine;

17) (S)-4-(N,N-di-n-pentylcarbamoyl)-1-(N,N-diphenylcarbamoyl)-2-(2-(N-methylamino)-N-(methyl)ethylaminocarbonyl)piperazine trifluoroacetic acid salt;

18) (S)-2-(2-(1-piperidinyl)ethylaminocarbonyl)-1-[N-(3-chlorophenyl)-N-phenylcarbamoyl]-4-(N,N-di-n-pentylcarbamoyl)piperazine;

19) <S)-2-(2-(1-piperidinyl)ethylaminocarbonyl)-4-(N,N-di-n-pentylcarbamoyl)-1-(N,N-diphenylcarbamoyl)piperazine;

20) (S)-2-(2-(N,N-bis(2-methoxybenzyl)amino)ethylaminocarbonyl)-1-(N,N-diphenylcarbamoyl)-4-(N,N-di-n-pentylcarbamoyl)piperazine;

21) (S)-4-(N,N-di-n-pentylcarbamoyl)-1-(N,N-diphenylcarbamoyl)-2-(2-(4-morpholinyl)ethylaminocarbonyl)piperazine;

22) (S)-2-(2-(N-benzyl-N-methylamino)-N-(methyl)ethylaminocarbonyl)-4-(N,N-di-n-pentylcarbamoyl)-1-(N,N-diphenylcarbamoyl)piperazine;

23) (S)-1-(N-(3-chlorophenyl)-N-phenylcarbamoyl)-2-(2-(N-methyl-N-(2-methoxybenzyl)amino)ethylaminocarbonyl)-4-(N,N-di-n-pentylcarbamoyl)piperazine;

24) (S)-2-(2-(N-(benzyloxycarbonyl)-N-(carbamoylmethyl)amino)-ethylaminocarbonyl)-4-(N,N-di-n-pentylcarbamoyl)-1-(N-(3-chlorophenyl)-N-phenylcarbamoyl)piperazine;

25) (S)-4-(N,N-di-n-pentylcarbamoyl)-1-(N-(3-chlorophenyl)-N-phenylcarbamoyl)-2-(2-(N-(2-methoxybenzyl)-N-(carbamoylmethyl)amino)-N-(methyl)ethylaminocarbonyl)piperazine;

26) (S)-1-(N-(3,5-dimethylphenyl)-N-phenylcarbamoyl)-2-(2-(N-methyl-N-(2-methoxybenzyl)amino)ethylaminocarbonyl)-4-(N,N-di-n-pentylcarbamoyl)piperazine;

27) (S)-1-(N-(3,5-dichlorophenyl)-N-phenylcarbamoyl)-2-(2-(N-methyl-N-(2-methoxybenzyl)amino)ethylaminocarbonyl)-4-(N,N-di-n-pentylcarbamoyl)piperazine;

28) (S)-4-(N,N-di-n-pentylcarbamoyl)-1-(N-(3,5-dichlorophenyl)-N-phenylcarbamoyl)-2-(2-N-(carbamoylmethyl)amino)ethylaminocarbonyl)piperazine;

29) (S)-4-(N,N-di-n-pentylcarbamoyl)-1-(N-(3,5-dichlorophenyl)-N-phenylcarbamoyl)-2-(2-(N-(2-methoxybenzyl)-N-(carbamoylmethyl)amino)ethylaminocarbonyl)piperazine;

30) (S)-4-(N,N-di-n-pentylcarbamoyl)-1-(N,N-diphenylcarbamoyl)-2-(2-N-(carbamoylmethyl)amino)ethylaminocarbonyl)piperazine;

31) (S)-4-(N,N-di-n-pentylcarbamoyl)-1-(N,N-diphenylcarbamoyl)-2-(2-(N-(2-methoxybenzyl)-N-(carbamoylmethyl)amino)ethylaminocarbonyl)piperazine;

32) (S)-4-(N,N-di-n-pentylcarbamoyl)-1-(N,N-diphenylcarbamoyl)-2-(2-N-(benzyloxycarbonylmethyl)amino)ethylaminocarbonyl)piperazine;

33) (S)-4-(N,N-di-n-pentylcarbamoyl)-1-(N,N-diphenylcarbamoyl)-2-(2-N-(benzyloxycarbonylmethyl)-N-methylamino)ethylaminocarbonyl)piperazine;

or a pharmaceutically acceptable salt thereof.

A second class of compounds within this embodiment are those compounds wherein:

$R^{1a}$ and $R^{1b}$ are independently H, $C_{1-8}$ alkyl or phenyl, either unsubstituted or substituted with —Cl, —Br, —I, —F, $C_{1-4}$ alkyl, or $C_{1-4}$ alkoxy;

$R^{2a}$ and $R^{2b}$ are independently phenyl, either unsubstituted or substituted with one or two substituents selected from the group consisting of:
1) —$C_{1-4}$ alkoxy,
2) —halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
 a) —halo,
 b) —OH,
 c) —$CF_3$,
 d) —$NH_2$,
 e) —NH($C_{1-4}$ alkyl),
 f) —N($C_{1-4}$ alkyl)($C_{1-4}$ alkyl)
 g) —$CO_2H$,
 h) —$CO_2$($C_{1-4}$ alkyl),
 i) $C_{1-4}$alkoxy,
 j) —$S(O)_x$($C_{1-4}$ alkyl) wherein x is 0, 1 or 2,
 k) —$C_{3-7}$ cycloalkyl;

and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$R^3$ is —$CO_2R^9$;

$R^4$ is H or is independently selected from the definitions of $R^3$;

$R^9$ is —$CH_2$-phenyl, wherein the phenyl is either unsubstituted or substituted with one or more substituents selected from the group consisting of:
1) —$C_{1-4}$ alkoxy,
2) —halo,
3) —OH,
4) —$CF_3$,
5) —$NH_2$,
6) —NH($C_{1-4}$ alkyl),
7) —N($C_{1-4}$ alkyl)$_2$,
8) —$CO_2H$, 9) —CO$_2$(C$_{1-4}$ alkyl), and
10) —C$_{1-6}$ alkyl, either unsubstituted or substituted with one or more substituents selected from the group consisting of:
 a) —halo,
 b) —OH,
 c) —CF$_3$,
 d) —NH$_2$,
 e) —NH(C$_{1-4}$ alkyl),
 f) —N(C$_{1-4}$ alkyl)(C$_{1-4}$ alkyl)
 g) —CO$_2$H,
 h) —CO$_2$(C$_{1-4}$ alkyl),
 i) C$_{1-4}$alkoxy,
 j) —S(O)$_x$(C$_{1-4}$ alkyl) wherein x is 0, 1 or 2,
 k) —C$_{3-7}$ cycloalkyl.

Specific compounds within this second class include:
1) 2-methoxybenzyl 4-(N,N-di-n-pentylcarbamoyl)-1-(N,N-diphenylcarbamoyl)-2-piperazinecarboxylate;
2) 3,5-bis-(trifluoromethyl)benzyl 4-(N,N-di-n-pentylcarbamoyl)-1-(N,N-diphenylcarbamoyl)-2-piperazinecarboxylate;
or a pharmaceutically acceptable salt thereof.

A third class of compounds within this embodiment are those compounds wherein:

R$^{1a}$ and R$^{1b}$ are independently H, C$_{1-8}$ alkyl or phenyl, either unsubstituted or substituted with —Cl, —Br, —I, —F, C$_{1-4}$ alkyl, or C$_{1-4}$ alkoxy;

R$^{2a}$ and R$^{2b}$ are independently phenyl, either unsubstituted or substituted with one or two substituents selected from the group consisting of:
1) —C$_{1-4}$ alkoxy,
2) —halo,
3) —OH,
4) —CF$_3$,
5) —NH$_2$,
6) —NH(C$_{1-4}$ alkyl),
7) —N(C$_{1-4}$ alkyl)$_2$,
8) —C$_2$H,
9) —CO$_2$(C$_{1-4}$ alkyl), and
10) —C$_{1-6}$ alkyl, either unsubstituted or substituted with one or more substituents selected from the group consisting of:
 a) —halo,
 b) —OH,
 c) —CF$_3$
 d) —NH$_2$,
 e) —NH(C$_{1-4}$ alkyl),
 f) —N(C$_{1-4}$ alkyl)(C$_{1-4}$ alkyl)
 g) —CO$_2$H,
 h) —CO$_2$(C$_{1-4}$ alkyl),
 i) C$_{1-4}$alkoxy,
 j) —S(O)$_x$(C$_{1-4}$ alkyl) wherein x is 0, 1 or 2,
 k) —C$_{3-7}$ cycloalkyl;

and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;

R$^3$ is C$_{1-6}$ alkyl substituted with one or more substituents selected from the group consisting of:
 a) —OH,
 b) —OR$^5$,
 c) —OCOR$^6$,
 d) —S(O)$_x$R$^5$,
 e) —OCONR$^5$R$^6$,
 f) —CONR$^5$R$^6$,
 g) —CO$_2$R$^6$,
 h) —N(R$^6$)CONR$^5$R$^6$,
 i) —NH$_2$,
 j) —NHR$^5$, or
 k) —NR$^5$R$^6$;

R$^5$ is C$_{1-6}$ alkyl either unsubstituted or substituted with one or more substituents selected from the group consisting of:
1) —halo,
2) —OH,
3) —CF$_3$
4) —NH$_2$,
5) —NH(C$_{1-4}$ alkyl),
6) —N(C$_{1-4}$ alkyl)$_2$,
7) —CO$_2$H,
8) —CO$_2$(C$_{1-4}$ alkyl),
9) —C$_{3-7}$ cycloalkyl,
10) phenyl, either unsubstituted or substituted with one or more of the substituents selected from the group consisting of:
 a) —C$_{1-4}$ alkyl,
 b) —halo,
 c) —OH,
 d) —C$_{1-4}$ alkoxy,
 e) —CF$_3$
 f) —NH$_2$,
 g) —NH(C$_{1-4}$ alkyl),
 h) —N(C$_{1-4}$ alkyl)(C$_{1-4}$ alkyl)
 i) —CO$_2$H,
 j) —CO$_2$(C$_{1-4}$ alkyl);

R$^6$ is —H or is independently selected from the definitions of R$^5$; or

R$^5$ and R$^6$ can be joined together to form with the nitrogen to which they are attached —N(CH$_2$CH$_2$)L, wherein L is selected from:
 i) a single bond,
 ii) —CH$_2$—,
 iii) —O—,
 iv) —S(O)$_p$—,
 v) —NH—,
 vi) —N—C$_{1-6}$alkyl;

R$^4$ is H or is independently selected from the definitions of R$^3$.

Specific compounds within this third class include:
1) 4-(N,N-di-n-pentylcarbamoyl)-1-(N,N-diphenylcarbamoyl)-2-(2-hydroxyethyl)piperazine;
2) 4-(N,N-di-n-pentylcarbamoyl)-1-(N,N-diphenylcarbamoyl)-2-[2-(3,5-bis(trifluoromethyl)benzyloxy)ethyl]piperazine;
3) 2-[2-((N-[2-((N'-benzyl-N'-methyl)amino)ethyl])-(N-methyl)amino)ethyl]-4-(N,N-di-n-pentylcarbamoyl)-1-(N,N-diphenylcarbamoyl)piperazine;
4) 2-[2-(N,N-diethylamino)ethyl]-4-(N,N-di-n-pentylcarbamoyl)-1-(N,N-diphenylcarbamoyl)piperazine;
5) 2-[2-(N,N-dibenzylamino)ethyl]-4-(N,N-di-n-pentylcarbamoyl)-1-(N,N-diphenylcarbamoyl)piperazine;
6) 2-[2-(N,N-di-n-propylamino)ethyl]-4-(N,N-di-n-pentylcarbamoyl)-1-(N,N-diphenylcarbamoyl)piperazine;
7) 2-[2-(N-[2-phenylethyl]amino)ethyl]-4-(N,N-di-n-pentylcarbamoyl)-1-(N,N-diphenylcarbamoyl)piperazine;
8) 2-[2-(1-[4-benzyl]piperazinyl)ethyl]-4-(N,N-di-n-pentylcarbamoyl)-1-(N,N-diphenylcarbamoyl)piperazine;
9) 2-[2-(N-benzylamino)ethyl]-4-(N,N-di-n-pentylcarbamoyl)-1-(N,N-diphenylcarbamoyl)piperazine;

10) 2-[2-(N-[4-phenylbutyl]amino)ethyl]-4-(N,N-di-n-pentylcarbamoyl)-1-(N,N-diphenylcarbamoyl)piperazine;

11) 2-[2-(3,5-dimethylbenzyloxy)ethyl]-4-(N,N-di-n-pentylcarbamoyl)-1-(N,N-diphenylcarbamoyl)piperazine;

12) 4-(N,N-di-n-pentylcarbamoyl)-1-(N,N-diphenylcarbamoyl)-2-(2-(3-phenylpropylamino)ethyl)piperazine;

13) 4-(N,N-di-n-pentylcarbamoyl)-1-(N,N-diphenylcarbamoyl)-2-(2-(2-(2-methoxyphenyl)ethylamino)ethyl)piperazine;

14) 2-(2-(2-(3,5-dimethylphenyl)ethylamino)ethyl)-4-(N,N-di-n-pentylcarbamoyl)-1-(N,N-diphenylcarbamoyl)piperazine;

or a pharmaceutically acceptable salt thereof.

Especially preferred compounds are those of structural formula I:

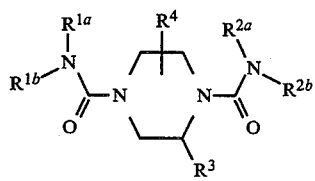

or a pharmaceutically acceptable salt thereof, wherein:

$R^{1a}$ is selected from the group consisting of:
1) $C_{5-6}$ alkyl,
2) phenyl,
3) —$CH_2$-phenyl, $R^{1b}$ is selected from the definitions of $R^{1a}$;

$R^{2a}$ and $R^{2b}$ are independently phenyl, either unsubstituted or substituted with one substitutent selected from the group consisting of:
1) —$OCH_3$,
2) —Cl,
3) —$CF_3$,
4) —$CH_3$;

$R^3$ is selected from the group consisting of:
1) —$CONR^7R^8$,
2) $C_{2-6}$alkyl substituted with one or more substituents selected from the group consisting of:
 a) —$NH_2$,
 b) —$NHR^5$,
 c) —$NR^5R^6$;

$R^4$ is H ;

$R^7$ is $C_{2-4}$ alkyl substituted with one substituent selected from the group consisting of:
1) 1) —$NHR^{10}$,
2) —$NR^{10}R^{11}$,
3) 4-morpholinyl,
4) 1-piperidinyl;

$R^8$ is H, $C_{1-6}$ alkyl or is independently selected from the definitions of $R^7$;

$R^{10}$ is —($C_{1-4}$ alkyl)-phenyl, wherein the phenyl is either unsubstituted or substituted with one or more substituents selected from the group consisting of:
1) —$OCH_3$,
2) —Cl,
3) —$CF_3$,
4) —$CH_3$, $R^{11}$ is $C_{1-6}$ alkyl, or is independently selected from the definitions of $R^{10}$.

The useful activities of the compounds of this invention are demonstrated and exemplified by the following assays.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% COat 37° C. until colonies were visible. Each colony was separated and propagated. The cell clone with the highest number of human NK1R was selected for subsequent applications such as drug screening.

C. Assay Protocol Using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ll of unlabeled substance p or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3H$-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

COGNITIVE DYSFUNCTION ASSAY

Efficacy of the present compounds to enhance cognitive function may be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces.

ANXIOLTYIC ASSAY

Anxiolytic activity of compounds may be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals.

DEPRESSION ASSAY

Antidepressant activity of compounds may be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods.

SCHIZOPHRENIA ASSAY

Antidopaminergic activity of the compounds may be demonstrated in an apomorphine-induced stereotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer.

The compounds of the present invention may antagonize the binding of angiotensin II to $AT_2$ receptors and be useful in treating disorders of the CNS which are attributed to the binding of angiontension II to $AT_2$ receptors. The compounds of this invention may also have central nervous system (CNS) activity and be useful in the treatment of cognitive dysfunctions including Alzheimer's disease, amnesia and senile sementia. These compounds may also have anxiolytic and antidepressant properties and be, therefore, useful in the relief of symptoms of anxiety and tension and in the treatment of patients with depressed or dysphoric mental states. In addition, these compounds may exhibit antidopaminergic properties and thus be useful to treat disorders that involve dopamine dysfunction such as schizophrenia. The compounds of the present invention may additionally be useful in treating conditions of the female reproductive system which result from the binding of angiotensin II to $AT_2$ receptors in reproductive organs. The compounds of the present invention may also be useful as anticancer agents for brain cancers and other cancers wherein the $AT_2$ receptor is prevelant.

The compounds of the present invention are useful in the prevention and treatment of a wide variety of clinical conditions which are characterized by the presence of an excess of tachykinin, in particular substance P, activity.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera such as ulcerative colitis, Crohn's disease and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions especially the transmission of pain in migraine. Hence, these compounds are readily adapted to therapeutic use for the treatment of physiological disorders associated with an excess of tachykinins, especially substance P, and as substance P antagonists the control and/or treatment of any of the aforesaid clinical conditions in mammals, including humans.

As calcium channel blocking agents some of the compounds of the present invention are useful in the prevention of treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrug resistance in tumor cells by enhancing the efficacy of chemotherapeutic agents. In addition, these compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced neruopathy; asthma; osteoarthritis; rheumatoid arthritis; and especially migraine.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of this invention may be administered to patients (animals and human) in need of such treatment in dosages that will provide optimal pharmaceutical efficacy. The dose will vary from patient to patient depending upon the nature and severity of disease, the patient's weight, special diets then being followed by a patient, concurrent medication, and other factors which those skilled in the art will recognize.

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. For example, in the treatment of conditions involving the neruotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

Several methods for preparing the compounds of this invention are illustrated in the following Schemes and Examples.

ABBREVIATIONS USED IN SCHEMES AND EXAMPLES

TABLE 1

Reagents:

TABLE 1-continued

| | |
|---|---|
| Et$_3$N | triethylamine |
| Ph$_3$P | triphenylphosphine |
| TFA | trifluoroacetic acid |
| NaOEt | sodium ethoxide |
| DCC | N,N'-dicyclohexylcarbodiimide |
| DCU | N,N'-dicyclohexylurea |
| CDI | 1,1'-carbonyldiimidazole |
| MCPBA | m-chloroperbenzoic acid |
| DBU | 1,8-diazabicyclo[5.4.0]undec-7-ene |
| Cbz-Cl | benzyl chloroformate |
| iPr$_2$NEt or DIEA | N,N diisopropylethylamine |
| NHS | N-hydroxysuccinimide |
| DIBAL | diisobutylaluminum hydride |
| Me$_2$SO$_4$ | dimethyl sulfate |
| HOBt | 1-hydroxybenzotriazole hydrate |
| EDAC | 1-ethyl-3-(3-dimethylaminopropyl)carbo-diimide hydrochloride |
| Solvents: | |
| DMF | dimethylformamide |
| THF | tetrahydrofuran |
| MeOH | methanol |
| EtOH | ethanol |
| AmOH | n-amyl alcohol |
| AcOH | acetic acid |
| MeCN | acetonitrile |
| DMSO | dimethylsulfoxide |
| Others: | |
| Ph | phenyl |
| Ar | aryl |
| Me | methyl |
| Et | ethyl |
| iPr | isopropyl |
| Am | n-amyl |
| Cbz | carbobenzyloxy (benzyloxycarbonyl) |
| Boc | tert-butoxycarbonyl |
| Trityl | triphenylmethyl |
| PTC | phase transfer catalyst |
| cat. | catalytic |
| FAB-MS | fast atom bombardment mass spectrometry |
| rt | room temperature |

For the synthesis of compounds of formula I, the central piperazine nucleus may be constructed by various methods. One such useful method, shown in Scheme 1, entails catalytic hydrogenation of a substituted pyrazine 1 to give the piperazine 2 [E. Felder, et al., *Helv. Chim. Acta*, 43, 888 (1960)]. This is typically accomplished by use of palladium on carbon as the catalyst, in a solvent such as ethanol or water, at a temperature of 20°-50° C.

SCHEME 1

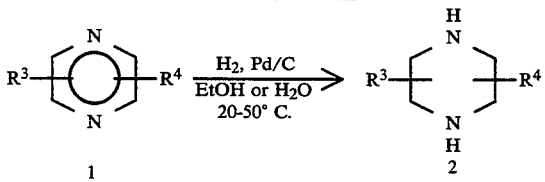

Another method (Scheme 2) involves reaction of a protected diamine 3 with a dibromo compound 4 in the presence of base at elevated temperature to give the bis-protected piperazine 5, which yields 2 upon deprotection. This method has been particularly useful in cases where 4 is a 2,3-dibromo ester. In the variation used by Piper, et al. [J. R. Piper, L. M. Rose, and T. P. Johnston, *J. Org. Chem.*, 37, 4476 (1972)], the protecting group P is p-toluenesulfonyl, and the disodium salt of 3 is heated with 4 (R=CO$_2$Et) in DMF at up to about 100°-110° C. to form the piperazine 5. The p-toluenesulfonyl protecting groups can be removed (along with simultaneous ester hydrolysis) by heating 5 at reflux in 48% HBr [F. L. Bach, Jr., et al., *J. Am. Chem. Soc.*, 77, 6049 (1955)]. In another variation [E. Jucker and E. Rissi, *Helv. Chim. Acta*, 45, 2383 (1962)], the protecting group P is benzyl, and heating 3 with 4 (R$^4$=CO$_2$Et) in benzene yields 5. In this case deprotection is achieved (without ester hydrolysis) by palladium-catalyzed hydrogenation in acetic acid.

SCHEME 2

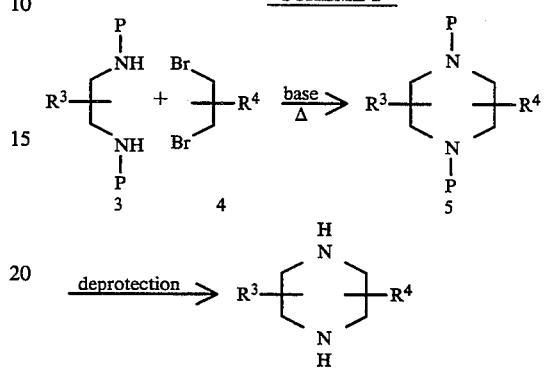

where P is a protecting group

Another route to piperazine-2-carboxylic acids is illustrated in Scheme 3. The α-Cbz-protected α,β-diamino ester 6 is reacted with α-bromo ester 7. Following hydrogenolyis of the Cbz group, the oxopiperazinecarboxylate 8 is obtained. Selective reduction and hydrolysis affords the piperazinecarboxylic acid 9. This route [B. Aebischer, et al., *Helv. Chim. Acta*, 72, 1043 (1989)] has been used (for R$^3$=H) to prepare chiral piperazine-2-carboxylic acid from a chiral diamino ester 6. Optically active piperazine-2-carboxylic acids have also been obtained from the racemate via a camphorsulfonic acid salt [E. Felder, *Helv. Chim. Acta*, 43, 888 (1960)3 or menthyl ester [B. Aebischer, et al., *Helv. Chim. Acta*, 72, 1043 (1989)].

SCHEME 3

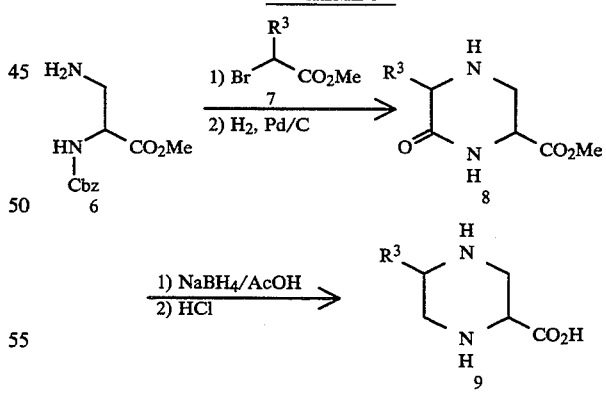

For the subclass of compounds of formula I wherein

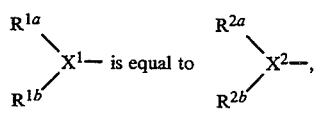

the acylation (or carbamoylation) of the piperazine nucleus may be accomplished straightforwardly in a single step. An example is shown in Scheme 4. Thus piperazine-2-carboxylic acid dihydrohalide (10) [F. L. Bach, Jr., et al., *J. Am. Chem. Soc.,* 77, 6049 (1955); E. Felder, et al., *Helv. Chim. Acta,* 43, 888 (1960)] in the presence of excess aqueous sodium hydroxide and a cosolvent such as acetonitrile may be treated with two equivalents of a carbamoyl chloride 11, preferably at about 0°–5° C. to afford the product 12. A similar reaction can be carried out with an acid chloride analogous to 11 in which N is replaced by CH.

where $R = R^{1a} = R^{2a}$,
$R' = R^{1b} = R^{2b}$ and
$X = Cl, Br, $ etc.

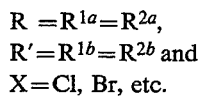

If $X^1$ does not equal $X^2$, the acylations (or carbamoylations, etc.) are performed in stepwise fashion. In the case of piperazine-2-carboxylic acid, a very useful method is to prepare a copper(II) complex, which blocks $N^1$ and allows the regiospecific synthesis of the $N^4$-Cbz derivative. After removal of copper(II), $N^1$ may then be acylated or carbamoylated. Upon deprotection to remove the Cbz group, $N^4$ is then available for introduction of a new acyl or carbamoyl group.

Such a pathway is illustrated in Scheme 5. By the method of M. E. Freed and J. R. Potoski [U.S. Pat. No. 4,032,639 (1977)], 10 is treated with basic cupric carbonate to generate the copper(II) complex, then reacted with Cbz-chloride in the presence of aqueous sodium bicarbonate and acetone, and finally treated with $H_2S$ gas in the presence of aqueous to break down the copper(II) complex, liberating 4-benzyloxycarbonyl)-2-piperazinecarboxylic acid (13). Variations include the use of cupric chloride at pH 9.5 to form the copper(II) complex and the use of Dowex 50 (H+ form) to ultimately remove the copper(II) ion. Treatment of 13 with acylating agent 14 in the presence of base (for example, aqueous sodium hydroxide in acetone or a tertiary amine in DMF or THF) gives 15. The Cbz group of 15 is removed by hydrogenation using palladium on carbon as catalyst in a solvent such as acetic acid, yielding 16. An alternative method of Cbz removal, the use of anhydrous HBr in acetic acid, is preferred when $R^{1a}$ and/or $R^{1b}$ in 15 contain functional groups unstable to hydrogenation. Next, 16 is treated with reagent 17 which may be, for example, a carbamoyl chloride, a carboxylic acid N-hydroxysuccinimide ester, an acyl imidazolide, or a carboxylic acid chloride. This reaction is preferably conducted in the presence of a tertiary amine base such as triethylamine or N,N-diisopropylethylamine in a solvent such as THF or DMF. The reaction is typically conducted at about 20°–50° C. or, in the case of a carboxylic acid chloride, at about 0° C., to give the product 18.

SCHEME 5

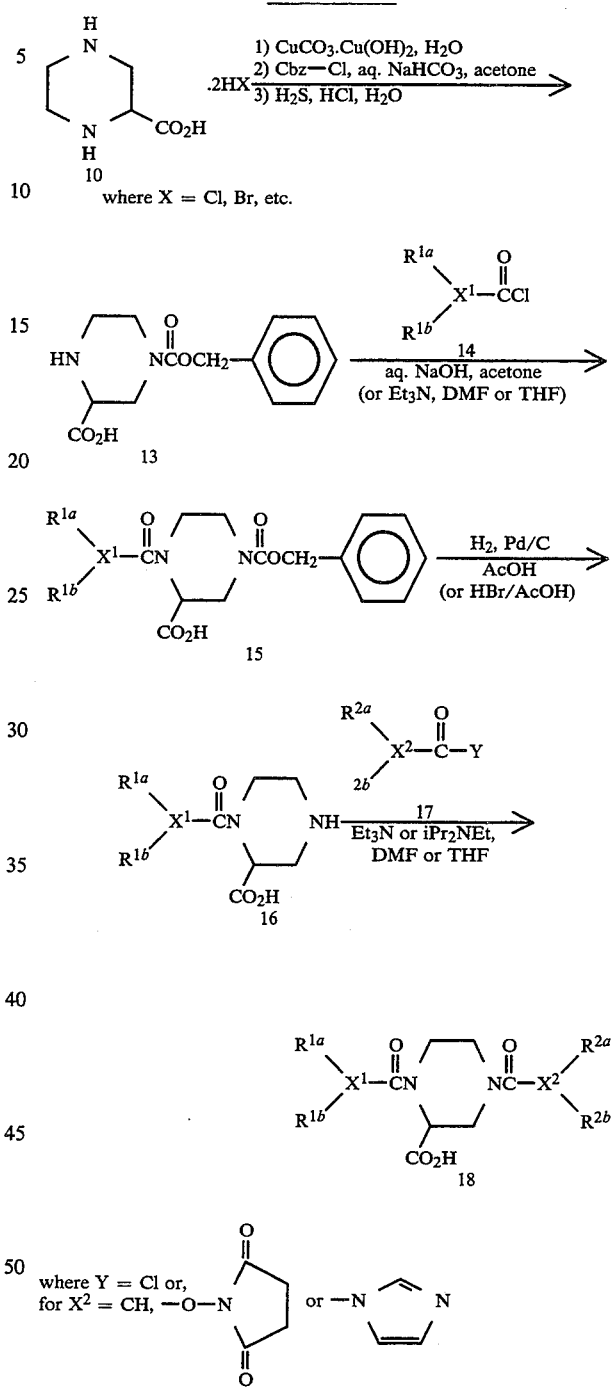

It is sometimes advantageous to avoid the intermediacy of Cbz protection in the synthesis of compounds of structure 18. In Scheme 6, a salt of piperazine-2-carboxylic acid (10) is converted in situ to the copper(II) complex and then treated directly with acylating agent 19 (equivalent to 17 where Y=Cl) in acetone in the presence of aqueous sodium hydroxide. Subsequent treatment with $H_2S$ in acetic acid at about 80° C. liberates 20. Reaction of 20 with acylating agent 14 (for example, in DMF in the presence of a base such as N,N-diisopropylethylamine) affords 18.

SCHEME 6

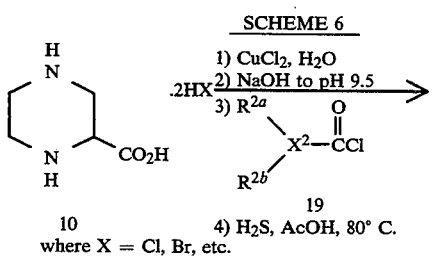

where X = Cl, Br, etc.

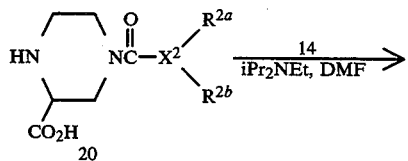

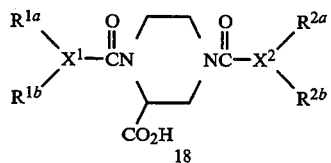

Mono-N-protected piperazine-2-carboxylate esters are also useful intermediates for the synthesis of compounds of formula I. Thus, intermediates 21 [H. Sugihara and K. Nishikawa, European Patent Application EP 368,670 (1990)], 22 (Sugihara and Nishikawa, op. cit.), 23 (Sugihara and Nishikawa, op. cit.), and 24 [C. F. Bigge, et Tetrahedron Lett., 30, 5193 (1989)] may all be subjected to an acylation-deprotection-acylation sequence to give 25, as shown in Scheme 7. Acylation (or carbamoylation, etc.) conditions are as described above. The Cbz group is generally removed by catalytic hydrogenation, as discussed above, whereas the Boc group is generally removed either with anhydrous trifluoroacetic acid (neat or in methylene chloride) or with anhydrous HCl in a solvent such as ethyl acetate.

SCHEME 7

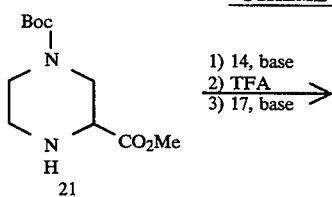

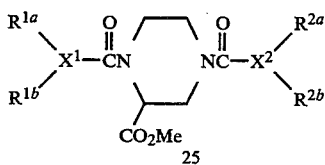

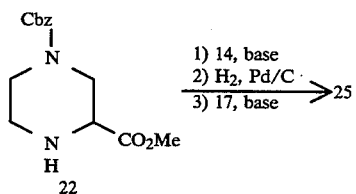

-continued
SCHEME 7

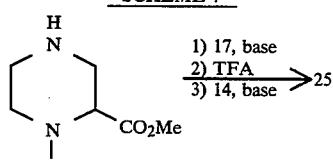

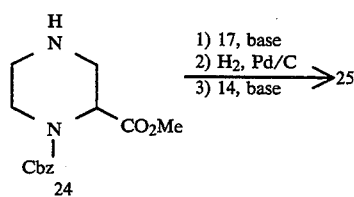

Reagents such as 14, 17, or 19 for acylation (or carbamoylation or oxycarbonylation) of the piperazine are prepared by methods well known in the literature. Several of these standard methods are shown in Scheme 8. For example, a secondary amine 26 is reacted with phosgene to give the carbamoyl chloride 27. The reaction may be carried out either by heating a solution of the amine and phosgene in toluene at about 90° C. or by conducting the reaction in a two-phase system of toluene and aqueous sodium hydroxide at about −5° C. In the case of primary amine 28 (equivalent to 26 where $R^b$=H), heating with phosgene in toluene yields the isocyanate 29, which can be reacted with a piperazine derivative in the same fashion as a carbamoyl chloride. One route to an N-aryl-N-alkyl(or aralkyl)carbamoyl chloride 33 is via reductive alkylation. Thus arylamine 30 and aldehyde 31. are reacted in the presence of sodium borohydride in a solvent such as ethanol to give the secondary amine 32, which is converted to 33 with phosgene as described above.

The N,N-diarylcarbamoyl chloride 33e is similarly obtained from the diarylamine 33d, which may be obtained via an Ullmann-type coupling. In one variant [cited in D. Schmidling and F. E. Condon, Baskerville Chem. J. City Coil. N.Y., 12, 22 (1963)], the acetanilide derivative 33a is reacted with aryl bromide 33b in the presence of copper and potassium carbonate in nitrobenzene at reflux to give the N,N-diaryl amide 33c, which is then hydrolyzed to 33d (for example, by heating with 70% sulfuric acid)[H. S. Freeman, J. R. Butler and L. D. Freedman, J. Org. Chem., 43, 4975 (1978)]. In another variant [D. Schmidling and F. E. Condon, op. cit.; S. Kurzepa and J. Cieslak, Roczniki Chem., 34, 111 (1960)], arylamine 30 is coupled with the orthobromobenzoic acid derivative 33f by heating at reflux in amyl alcohol in the presence of potassium carbonate and copper. The resulting product 33g, upon heating to about 220°–260° C., undergoes decarboxylation to 33d.

Chloroformate 35 is readily prepared from alcohol 34 with phosgene in toluene, typically at 0°–20° C. Carboxylic acid 36 may be converted to the acid chloride 37 by treatment with thionyl chloride (for example in benzene at 80° C.). Treatment of 36 with N-hydroxysuccinimide (NHS) in the presence of N,N,-dicyclohexylcarbodiimide (DCC) in a solvent such as acetonitrile provides the reactive N-hydroxysuccinimide ester. The acylimidazolide 39, also a useful acylating agent which may be prepared in situ, is obtained by treatment of 36 with 1,1'-carbonyldiimidazole (CDI) in a solvent such as THF.

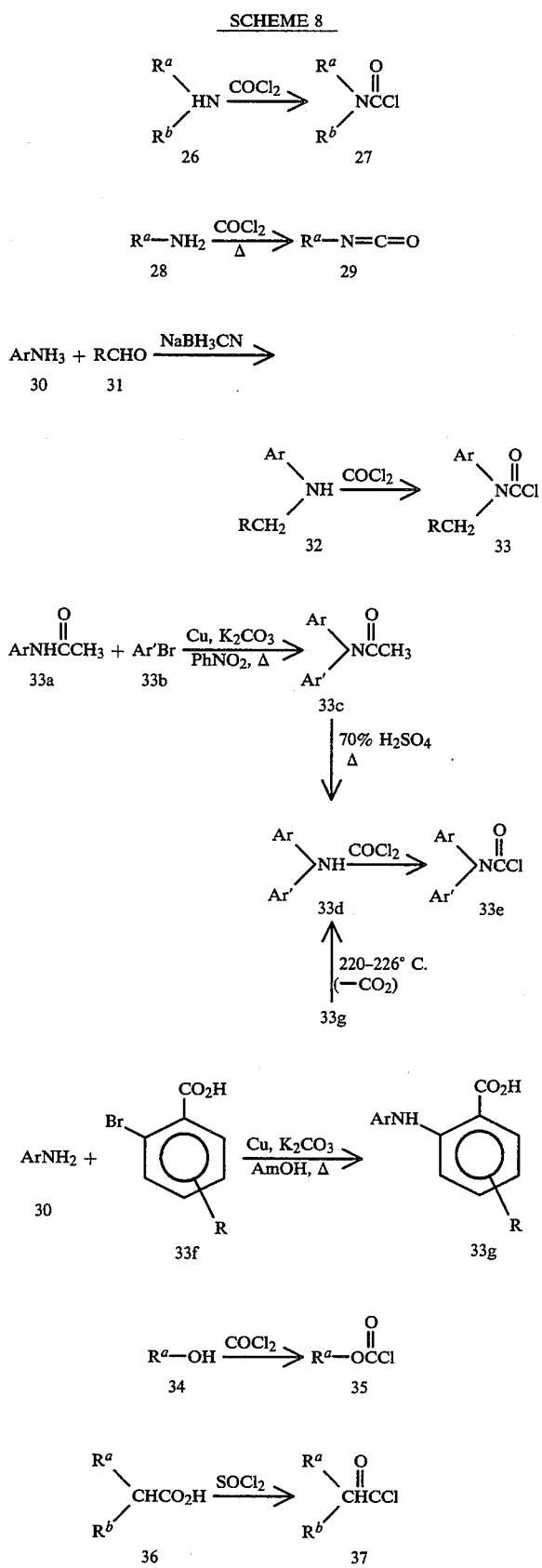

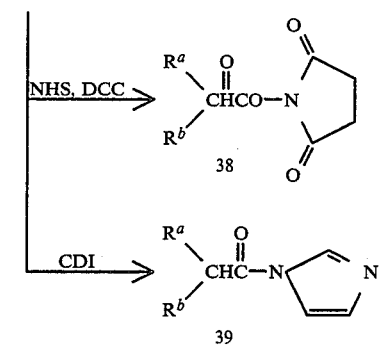

In compounds of formula 1, the $R^3$ and $R^4$ substituents may be present at the time the piperazine ring system is formed, as shown in Schemes 1-3. However, additional transformations may be carried out on the $R^3$ and/or $R^4$ functional groups after elaboration of the diacylated (or carbamoylated, etc.) piperazine. For example, as shown in Scheme 9, piperazinecarboxylic acid 40 may be readily converted to its methyl ester 41 by treatment with diazomethane, preferably in ether-methanol or THF at 0°–25° C. [B. Aebischer, et al., Helv. Chim. Acta, 72, 1043 (1989); C. F. Bigge, et al., Tetrahedron Lett., 30, 5193 (1990)] or by other methods (C. F. Bigge, et al., op. cit.). The acid 40 may also be obtained by saponification of 41 under standard conditions. The methyl ester 41 may also be reduced to alcohol 42 by treatment with sodium borohydride/methanol according to the procedures of Sugihara and Nishikawa (EP 368,670). Treatment of carboxylic acid 40 with DCC (or with 1-(3-dimethyl-aminopropyl)-3-ethylcarbodiimide hydrochloride in the presence of HOBT) followed by amine 43 affords the amide 44. Methyl ester 41 may be transformed to aldehyde 45 by use of diisobutylaluminum hydride under controlled conditions at −78° C. Alternatively, alcohol 42 can be oxidized to 45 by various methods, such as the use of catalytic tetrapropylammonium perruthenate (TPAP) and 4-methylmorpholine N-oxide (NMO) in the presence of molecular sieves [W. P. Griffith, et al., J. Chem. Soc. Chem. Commun., 1625 (1987)]. Using standard reductive alkylation conditions, 45 is reacted with amine 43 in the presence of sodium cyanoborohydride to give the aminomethylpiperazine 46. Alcohol 42 may be converted to methyl ether 47 by use of dimethyl sulfate, 50% aqueous sodium hydroxide, and a phase transfer catalyst (PTC) such as tetrabutylammonium hydrogen sulfate [A. Metz, Angew. Chem. Int. Ed. Engl., 12, 846 (1973).

The acylsulfonamide derivative 48 is obtained by treating the carboxylic acid 40 with carbonyldiimidazole and then with the sulfonamide, $RSO_2NH_2$, and DBU as base in a solvent such as THF. Treatment of alcohol 42 with the carbamoyl chloride 49 in the presence of a base such as N,N-diisopropylethylamine yields the carbamate 50. Similarly, reaction of 42 with acid chloride 51 in the presence of a base like pyridine gives the acyloxymethylpiperazine 52. The bromomethyl intermediate 53 is available by treatment of alcohol 42 with triphenylphosphine and carbon tetrabromide. Displacement of the bromo group by a thiol 54 occurs in the presence of N,N-diisopropylethylamine as base to give the thioether 55. Oxidation of 55 to the sulfoxide 56 or the sulfone 57 may be carried out with m-chloroperbenzoic acid (MCPBA) in a solvent such as methylene chloride or acetic acid. Whether 56 or 57 is the major or exclusive product is dependent on the stoichiometry, reaction time, and temperature.

Besides the methyl ester 41, the carboxylic acid 40 may be converted into other esters 58, for example by treatment with carbonyldiimidazole and an alcohol, ROH, in the presence of catalytic sodium ethoxide [H. A. Staab and A. Mannschreck, Chem. Ber., 95, 1284 (1962)]. An α-(acyloxy)alkyl ester 60 may be obtained by reaction of 40 with an α-chloralkyl ester 59 in the presence of triethylamine, sodium iodide, and tetrabutylammonium hydrogen sulfate as phase transfer catalyst [E. W. Petrillo, et al., U.S. Pat. No. 4,873,356 (1989)].

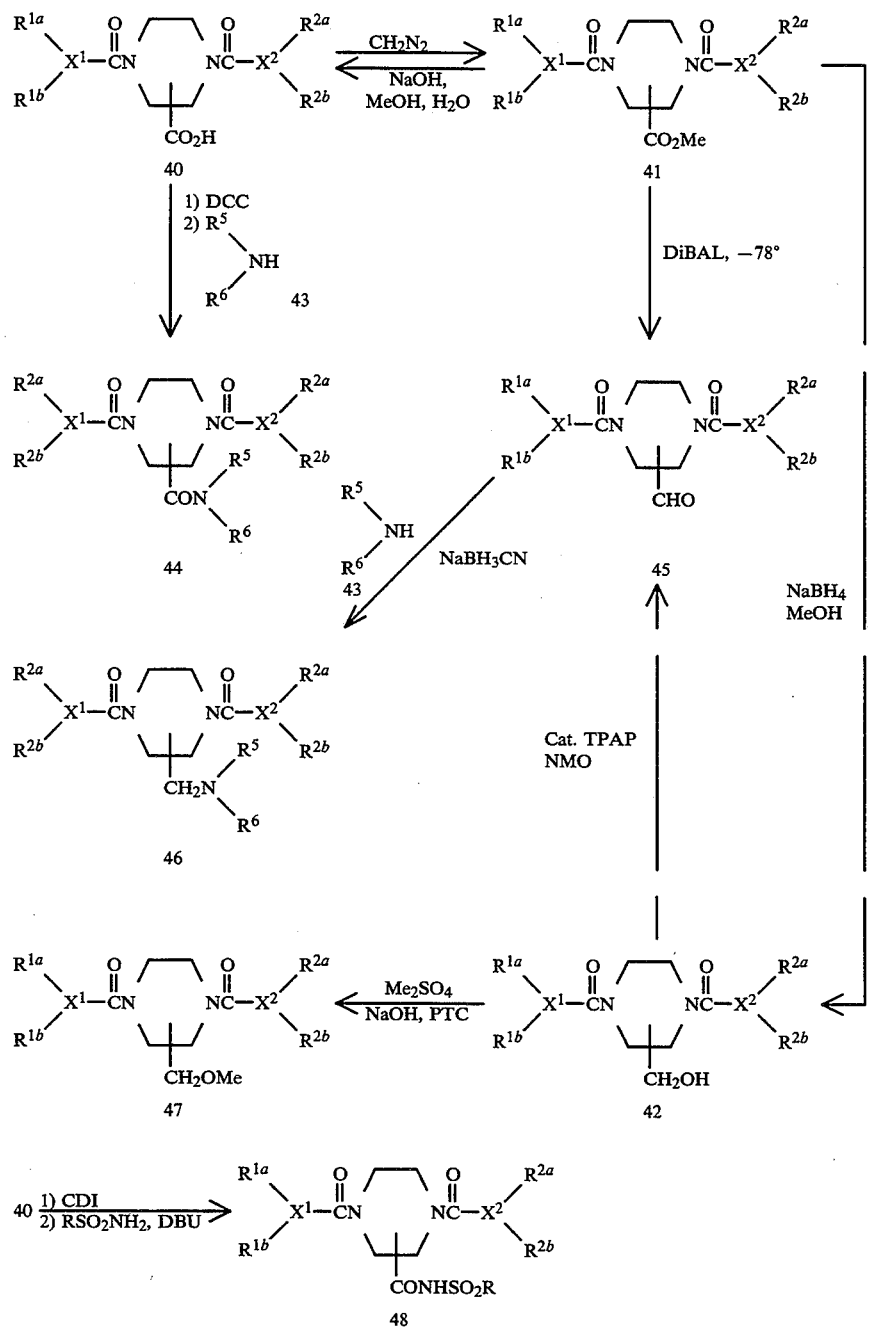

SCHEME 9

SCHEME 9
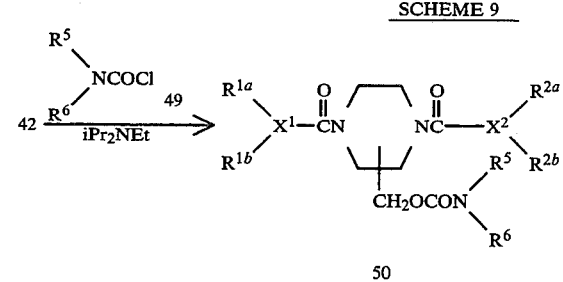
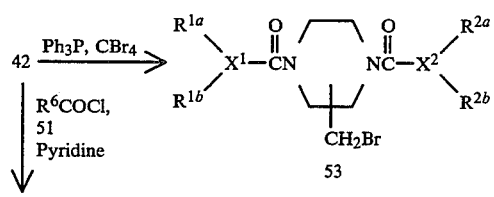
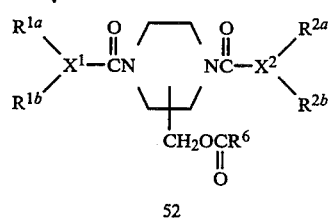
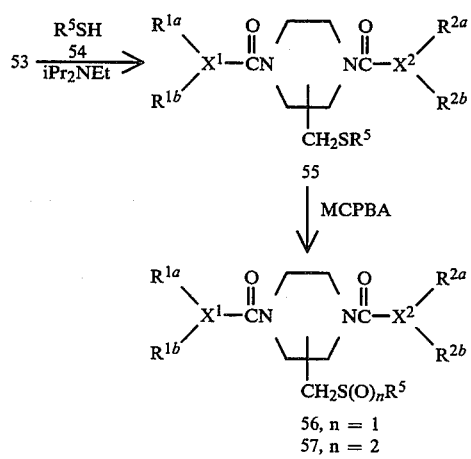
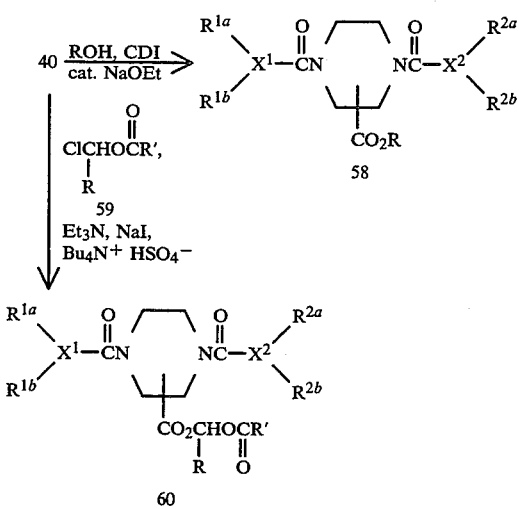
Preparation of 2-(2-hydroxyethyl)piperazines and 2-(2-aminoethyl)piperazines can be carried out as illustrated in Scheme 10. Treatment of 2-methylpyrazine with paraformaldehyde at 165° C. (as described by Kitchen and Hanson, *J. Am. Chem, Soc.*, 1951, 73, 1838) provides hydroxyethyl derivative 61, which may be reduced to 2-(2-hydroxyethyl)piperazine by hydrogenation in the presence of a platinum catalyst. Selective protection with trityl chloride provides the bis-protected compound 62. Acylation with the appropriate carbamoyl chloride then gives 63, which may be deprotected to amino alcohol 64. Acylation with a second carbamoyl chloride produces 65, which may be converted to bromide 66 with triphenyphosphine dibromide. Treatment with the appropriate amine or alcohol leads to the corresponding substituted amines 67 or ethers 68, respectively.

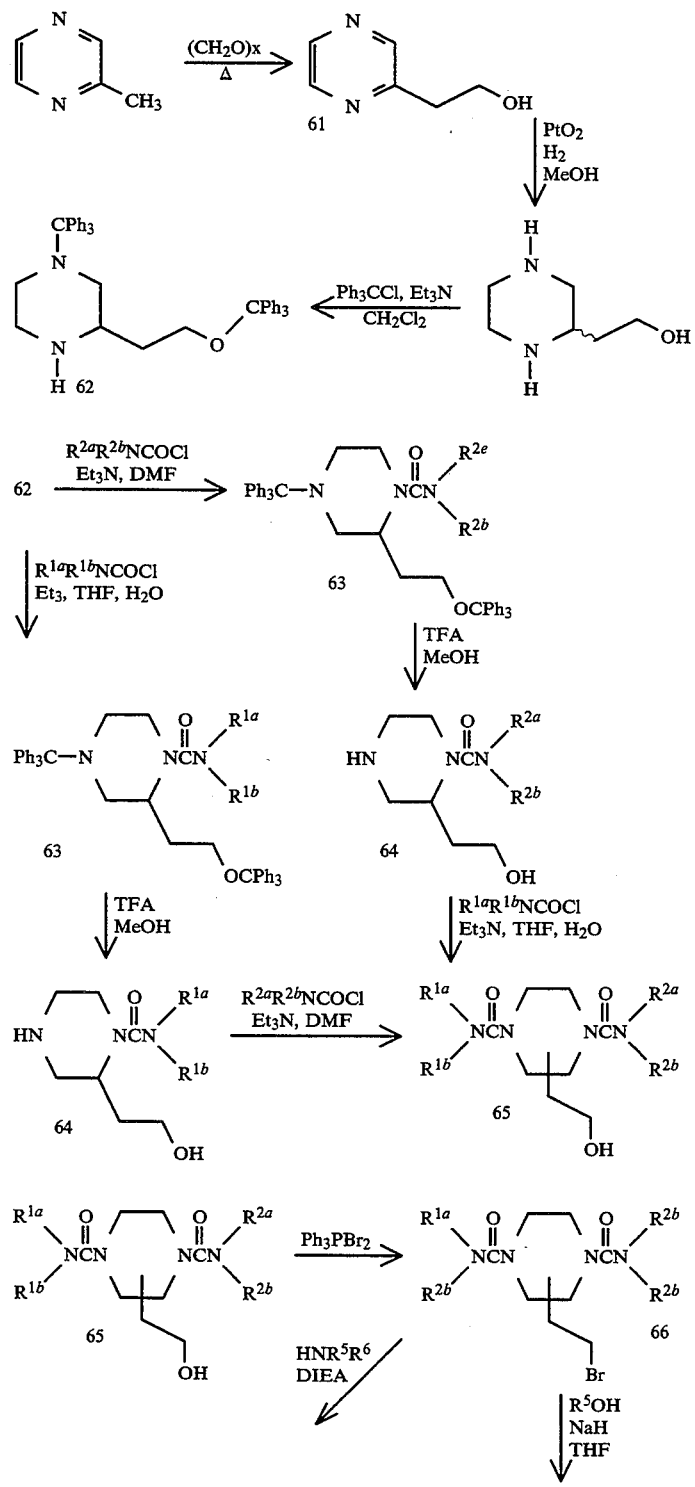

SCHEME 10

SCHEME 10

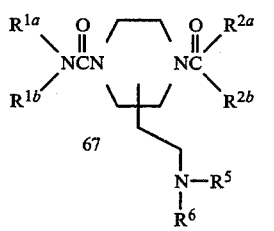 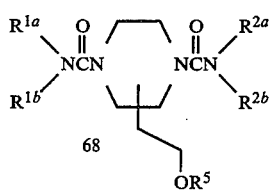

-continued

The object compounds of Formula I obtained according to the reactions as explained above can be isolated and purified in a conventional manner, for example, extraction, precipitation, fractional crystallization, recrystallization, chromatography, and the like.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Although the reaction schemes described herein are reasonably general, it will be understood by those skilled in the art of organic synthesis that one or more functional groups present in a given compound of formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

The following examples are given for the purpose of illustrating the present invention and shall not be construed as being limitations on the scope or spirit of the invention.

EXAMPLE 1

2-(2-(N-Methyl-N-(2-methoxybenzyl)amino)ethylaminocarbonyl)-4-(N,N-di-n-pentylcarbamoyl)-1-(N,N-diphenylcarbamoyl)piperazine Step A:
(S)-4-(Benzyloxycarbonyl)piperazine-2-carboxylic acid A solution of 16.4 g (27.6 mmole) of (S)-piperazine-2-carboxylic acid.2 camphorsulfonic acid [E. Felder, S. Maffei, S. Pietra and D. Pitre, *Helv. Chim. Acta,* 43, 888 (1960)]* in 60 ml of water was treated with 2,0 g (14.9 mmole) of cupric chloride to give a light blue solution. 4.16 g (52 mmole) of 50% sodium hydroxide was added to raise the pH to 9.5 giving a deep blue colored solution. A 60 ml portion of acetone was added and the solution was cooled to 0° C. with mechanical stirring. While at 0°, a solution of 6.0 g (33.4 mmole) of 95% benzyl chloroformate in 28 ml of acetone and 28 ml (28 mmole) of 1N sodium hydroxide were added at equal rates over 2 hours to give a slurry of light blue solid in a deep blue solution. After centrifuging, the solid was stirred with 200 ml of 1:1 ethanol-water and was acidified to pH 3 with 6N HCl. The light blue solution was applied to 200 cc of Dowex 50 (H+) which was washed with 900 ml of 1:1 ethanol-water until no longer acid. The column was washed with 600 ml of 6:97:97 pyridine-ethanol-water, and the product was eluted with 800 ml of the same solvent. The solution was concentrated to 200 ml in vacuo and the slurry was lyophilized to give 5.09 g (70%) of white solid, mp 198°–200° C. dec., homogeneous by TLC (1:1:1:1 n-butyl alcohol-acetic acid-water-ethyl acetate, $R_f$=0.75; 80:20:2 chloroform methanol-ammonia water, $R_f$=0.30).

Mass spectrum (FAB): m/e 265 (M+1).

$^1$H NMR (DMSO-$d_6$, 400 MHz, ppm): δ 2.82 (t of d, 1H), 3.0–3.1 (m, 3H), 3.26 (d of d, 1H) , 3.89 (d, 1H), 4.19 (d, 1H), 5.08 (s, 2H), 7.3–7. 4 (m, 5H).

*Note: The "(-)-piperazine-2-carboxylic acid" obtained by this literature procedure was converted to its dihydrochloride salt, having [α]$_D$= −5.24° (c=1.25, H$_2$O). This is essentially equal and opposite in sign to the rotation reported for (R)-piperazine-2-carboxylic acid dihydrochloride prepared from a chiral starting material of known absolute configuration [B. Aebischer, et al., *Helv. Chim. Acta,* 72, 1043 (1989)]. Thus the configuration of the (-)-piperazine-2-carboxylic acid used here is assigned as (S).

Step B:
(S)-4-(Benzyloxycarbonyl)-1-(diphenylcarbamoyl)piperazine-2-carboxylic acid A solution of 1.03 g (3.90 mmole) of (S)-4-(benzyloxycarbonyl)piperazine-2-carboxylic acid (from Step A) in 12 ml. of DMF was treated with 0.788 g (7.79 mmole)

of triethylamine at 25° C. With stirring 0.901 g (3.89 mmole) of diphenylcarbamoyl chloride was added in portions over 2 hours. After 16 hours the mixture was concentrated in vacuo to an orange oil which was chromatographed over an 88×2.5 cm LH 20 column with 11 ml. fractions of methanol. Fractions 35–43 were combined and concentrated to 1.136 g (64%) of pale yellow oil which contained a major spot by TLC (80:18:2 chloroform-methanolammonia water, $R_f$=0.45).

Mass spectrum (FAB): m/e 460 (M+1).

$^1$H NMR (CDCl$_3$, 300 MHz, ppm): δ 2.65 (br m, 1H), 3.03 (d of d, 1H), 3.15 (m, 1H), 3.58 (d, 1H), 3.80 (d, 1H), 4.52 (d, 1H), 4.73 (s, 1H), 5.12 (s, 2H), 7.03–7.45 (m, 15H).

Step C:
(S)-1-(Diphenylcarbamoyl)piperazine-2-carboxylic acid acetate salt A solution of 1.136 g (2.47 mmole) of (S)-4-(benzyloxycarbonyl)-1-(diphenylcarbamoyl)piperazine-2-carboxylic acid (from Step B) and 0.5 ml of acetic acid in 10 ml of methanol was treated with 0.50 g of 10% Pd/C, and the mixture was hydrogenated at 40 psi with rocking for 10 hours. The mixture was filtered and the catalyst was washed with 40 ml of acetic acid at 60° C. The organics were combined, concentrated in vacuo and flushed with 3×40 ml of ethyl acetate to give 0.73 g (76%) of white solid which was homogeneous by TLC (1:1:1:1 n-butyl alcohol:acetic acid-water-ethyl acetate, $R_f$=0.70; 80:18:2 chloroform-methanol-ammonia water, $R_f$=0.10).

Mass Spectrum (FAB): m/e 326 (M+1).

$^1$NMR (DMSO-d$_6$, 200 MHz, ppm): δ 1.90 (s, 3H), 2.9–3.7 (m, 6H), 4.19 (br. s, 1H), 7.02–7.17 (m, 6H), 7.27–7.38 (m, 4H).

Step C-2: Dipentylcarbamoyl chloride

A mixture of 7.86 g. (50.0 mmole) of dipentylamine, 18.05 ml (50.0 mmole) of 2.77M NaOH solution and 60 ml of toluene was vigorously stirred at −7° to −5° C., and 60 ml (115.8 mmole) of 1.93M phosgene in toluene was added dropwise over 1 hour. After stirring an additional 30 min., the cold mixture was separated and the toluene layer was dried over solid NaCl. After filtering, nitrogen was bubbled through the solution for 1 hour and the solution was concentrated in vacuo to 10.5 g. (95%) of light yellow oil.

IR (cm$^{-1}$): 1740.

Mass spectrum (FAB); m/e 220 (M+1).

$^1$NMR (CDCl$_3$, 400 MHz, ppm): δ 0.91 (overlapping t, 6H), 1.25–1.38 (m, 2H), 1.53–1.67 (m, 4H), 3.32 (t, 2H), 3.37 (t, 2H).

Step D:
(S)-4-(Dipentylcarbamoyl)-1-(diphenylcarbamoyl)piperazine-2-carboxylic acid A mixture of 0.73 g (2.05 mmole) of (S)-1-(diphenylcarbamoyl)piperazine-2-carboxylic acid acetate salt (from Step C) and 0.59 g (5.83 mmole) of triethylamine in 15 ml of DMF was treated with dipentylcarbamoyl chloride (Step C-2) under nitrogen at 50° C. with stirring for 2 hours to give a clear solution. The DMF was removed in vacuo over a 50° C. bath to leave a yellow oil which was partitioned between 100 ml of 0.2N HCl and 125 ml of ethyl acetate. After drying over sodium sulfate the ethyl acetate was removed in vacuo to leave a dark yellow, gummy material which was flash chromatographed over 100 cc of silica gel with 16×15 ml fractions of 1:1 (hexane:ethyl acetate) and with 15 ml fractions of methanol. Methanol fractions 5–11 were combined and concentrated. The residue was applied to an 85×2.5 cm LH-20 column and eluted with 11 ml fractions of methanol. Fractions 33–38 were combined, concentrated and rechromatographed over LH-20 exactly as before. Fractions 33–39 were combined and concentrated to 124 mg (12%) of glassy gum, homogeneous by TLC (80:20:2 chloroform-methanolammonia water, $R_f$=0.5).

Mass spectrum (FAB): m/e 509 (M+1).

Analysis (C$_{29}$H$_{40}$N$_4$O$_4$·0.4 H$_2$O): Calculated: C, 67.45; H, 7.91; N, 10.85 Found: C, 67.70; H, 8.03; N, 10.65. $^1$H NMR (CDCl$_3$, 400 MHz, ppm): δ 0.85 (t, 6H), 1.19 (m, 4H), 1.27 (m, 4H), 1.46 (m, 4H), 2.63 (t of d, 1H), 2.91 (d of d, 1H), 3.11 (m, 5H), 3.23 (m, 1H), 3.62 (m, 1H), 3.89 (d, 1H), 4.72 (s, 1H), 7.11 (d, 4H), 7.14 (t, 2H), 7.29 (t, 4H).

Step E:
(S)-2-[(2-aminoethyl)aminocarbonyl]-4-(N,N-di-N-pentylcarbamoyl)-1-(N,N-diphenylcarbamoyl)piperazine A mixture of 202 mg (0.4 mmole) of (S)-1-(N,N-diphenylcarbamoyl)-4-(N,N-di-n-pentylcarbamoyl)piperazine-2-carboxylic acid and 59 mg (0.44 mmole) of HOBt in 4 mL of CH$_2$Cl$_2$ was cooled to 0° C. and was treated with 107 mg (0.56 mmole) of EDAC. After 5 min, the cooling bath was removed and after an additional 30 min, the mixture was cooled to −33° C. and was treated with 398 microliters (5.96 mmole) of ethylenediamine. After 10 min the cooling bath was removed and the mixture stirred at 22° C. for 24 hours. Most of the volatiles were removed by a gentle stream of nitrogen and the residue was purified by flash chromatography on 23 g of silica gel eluting with 1 liter of 100:9:0.4 CH$_2$Cl$_2$:MeOH:ammonia water to give 125 mg (57%) of an oil.

Mass Spectrum (FAB): m/Z 706 (M+matrix, 40%), 551 (M+H, 100%), 196 (60%).

$^1$H NMR (CDCl$_3$, 400 MHz, ppm): δ 0.85 (t, 6H), 1.05 (br s, 2H), 1.1–1.3 (m, 8H), 1.45 (quintet, 4H), 2.7–2.85 (m, 4H), 2.9–3.1 (3H), 3.15–3.3 (5H), 3.73 (br d, 1H), 3.97 (d, 11{), 4.50 (s, 1H), 7.1–7.15 (6H), 7.25–7.33 (4H), 7.46 (br t, 1H).

Step F:
(S)-2-(2-(N-(2-Methoxybenzyl)amino)ethylaminocarbonyl)-4-(N,N-di-n-pentylcarbamoyl)-1-(N,N-diphenylcarbamoyl)piperazine A solution of 82 mg (0.15 mole) of (S)-2-[(2-aminoethyl)aminocarbonyl]-4-(N,N-di-n-pentylcarbamoyl)-1-(N,N-diphenylcarbamoyl)piperazine and 22 mg (0.16 mole) of o-anisaldehyde in 1.5 mL of MeOH was treated with 9 mg (0.15 mmole) of sodium cyanoborohydride. To this solution was added dropwise 5% acetic acid in acetonitrile until the pH of the solution was between 6.0–6.5 (as measured by spotting onto wet pH paper). After 16 hours most of the solvent was gently removed in a stream of nitrogen and the residue was purified by flash chromatography on 23g of silica gel eluting with 100:6:0.4 CH$_2$Cl$_2$:MeOH: ammonia water to give 39 mg (39%) of an oil.

Mass Spectrum (FAB): m/Z 672 (M+H, 100%), 196 (30%), 121 (65%).

$^1$H NMR (CDCl$_3$, 400 MHz, ppm): δ 0.85 (t, 6H), 1.15–1.3 (m, 8H), 1.45 (quintet, 4H), 2 (v br s, 1H), 2.65–2.77 (m, 3H), 2.83 (dd, 1H), 3.0–3.1 (m, 3H), 3.13–3.23 (m, 3H), 3.32 (apparent nonet, 2H), 3.70 (d, 1H), 3.78 (s, 2H), 3.81 (s, 3H), 3.96 (d, 1H), 4.53 (br s, 1H), 6.83–6.90 (m, 2H), 7.08–7.3 (m, 13H).

Step G:
(S)-2-(2-(N-Methyl-N-(2-methoxybenzyl)amino)ethylaminocarbonyl)-4-(N,N-di-n-pentylcarbamoyl)-1-(N,N-diphenylcarbamoyl)piperazine A solution of 38 mg (0.057 mmole) of 2-(2-(N-(2-methoxybenzyl)amino)ethylaminocarbonyl)-4-(N,N-di-n-pentylcarbamoyl)-1-(N,N-diphenylcarbamoyl)piperazine and 23 microliters (0.28 mmole) of 37% aqueous formaldehyde was treated with 6 mg (0.091 mmole) of sodium cyanoborohydride at 22° C. and was stirred for 15 min. To this solution was added dropwise 5% acetic acid in acetonitrile until the pH of the solution was between 6.5–7.0 (as measured by spotting onto wet pH paper). Additional aliquots of the acetic acid/acetonitrile mixture were added as necessary over the next 40 min to maintain the pH between 6.5–7.0. One mL of MeOH was added, and after two min most of the solvent was gently removed in a stream of nitrogen. The residue was purified by flash chromatography on 23 g of silica gel eluting with 500 mL of 100:3:0.2 $CH_2Cl_2$:MeOH: ammonia water to give 34 mg (87%) of an oil.

Mass Spectrum (FAB): m/Z 685 (M+H, 100%); 196 ($Ph_2NCO$, 15%); 164 ($MeOPhCH_2N(Me)CH_2$, 25%); 121 ($MeOPhCH_2$, 65%).

$^1$H NMR ($CDCl_3$, 400 MHz, ppm): δ 0.85 (t, 6H), 1.1–1.3 (m, 8H), 1.44 (quintet, 4H), 2.2 (br s, 3H), 2.52 (br s, 2H), 2.67 (t, 1H), 2.80 (dd, 1H), 3.0–3.2 (m, 6H), 3.31 (m, 1H), 3.39 (m, 1H), 3.55 (br s, 2H), 3.73 (d, 1H), 3.79 (s, 3H), 3.89 (d, 1H), 4.52 (br s, 1H), 6.86 (m, 2H), 6.94 (br s, 1H), 7.05–7.15 (m, 6H), 7.2–7.3 (m, 6H).

EXAMPLE 2

(S)-4-(N,N-Di-n-pentylcarbamoyl)-1-(N,N-diphenylcarbamoyl)-2-(2-(N-methyl-N-(2-methoxybenzyl)amino)-N-(methyl)ethylaminocarbonyl)piperazine

Step. A:
N-Methyl-N'-methyl-N'-t-butoxycarbonylethylenediamine

A solution of 1 gram (4.58 mmole) of di-t-butyl-dicarbonate in 8 mL of $CH_2Cl_2$ at 0° C. was treated with 0.98 mL (9.16 mmole) of N-methyl-N'-methylethylenediamine. After 20 min the cooling bath was removed and the mixture allowed to warm to 22° C. After 4 hours the mixture was concentrated in vacuo. The residue was purified by flash chromatography on 68 g silica gel eluting with 1 liter of 100:9:0.3 $CH_2Cl_2$:MeOH: ammonia water, then 500 mL of 100:11:0.3 $CH_2Cl_2$:MeOH: ammonia water to give 190 mg (22%) of a volatile oil.

Step B:
(S)-4-(N,N-Di-n-pentylcarbamoyl)-1-(N,N-diphenylcarbamoyl)-2-(2-(N-methyl-N-(t-butoxycarbonyl)amino)-N-(methyl)ethylaminocarbonyl)piperazine According to the procedure of Example 1, Step E above, 127 mg (0.25 mmole) of (S)-1-(N,N-di-phenylcarbamoyl)-4-(N,N-di-n-pentylcarbamoyl)piperazine-2-carboxylic acid, 37 mg (0.27 mmole) of HOBt, 67 mg (0.35 mmole) of EDAC, and 94 mg (0.50 mmole) of N-methyl-N'-methyl-N'-t-butoxycarbonylethylenediamine after purification by flash chromatography on 24 g of silica gel with 100:2: $CH_2Cl_2$:MeOH provided 144 mg (85%) of an oil.

Mass Spectrum (FAB): m/Z 679 (M+H,80%), 579 (M-Boc, 60%), 491 (M—$MeN(CH_2)_2N(Me)Boc$, 100%).

Step C:
(S)-4-(N,N-Di-n-pentylcarbamoyl)-1-(N,N-diphenylcarbamoyl)-2-(2-(N-methylamino)-N-(methyl)ethylaminocarbonyl)piperazine trifluoroacetic acid salt To a mixture of 130 mg (0.19 mmole) of 4-(N,N-di-n-pentylcarbamoyl)-1-(N,N-diphenylcarbamoyl)-2-(2-(N-methyl-N-(t-butoxycarbonyl)amino)-N-(methyl)ethylaminocarbonyl)piperazine and 0.4 mL of anisole at 0° C. was added 2 mL of trifluoroacetic acid precooled to 0° C. After 45 min the solution was concentrated in vacuo and the residue purified by flash chromatography on 16 g of silica gel eluting with 100:9 $CH_2Cl_2$:MeOH to give 130 mg (98%) of an oil.

Mass Spectrum (FAB): m/Z 579 (M+H,100%).

Step D:
(S)-4-(N,N-Di-n-pentylcarbamoyl)-1-(N,N-diphenylcarbamoyl)-2-(2-(N-methyl-N-(2-methoxybenzyl)amino)-N-(methyl)ethylaminocarbonyl)piperazine A solution of 41 mg (0.059 mmole) of 4-(N,N-di-n-pentylcarbamoyl)-1-(N,N-diphenylcarbamoyl)-2-(2-(N-methylamino)-N-(methyl)ethylaminocarbonyl)piperazine trifluoroacetic acid salt, 23 microliters (0.133 mmole) of DIEA and 9 mg (0.059 mole) of 2-methoxybenzyl chloride (as a 50% solution in $CHCl_3$) in 1 mL of MeCN was stirred for 4 days at 22° C. The solution was concentrated in vacuo and the residue purified by flash chromatography on 16 g of silica gel eluting with 100:4:0.1 $CH_2Cl_2$:MeOH:ammonia water to give 25 mg (61%) of an oil.

Mass Spectrum (FAB): m/Z 699 (M+H,100%), 579 (15%), 196 (80%).

$^1$H NMR ($CDCl_3$, 400 MHz, ppm): δ 0.85 (m, 6H), 1.1–1.3 (m, 8H), 2.43 (br sextet, 4H), 2.2–2.3 (major and minor br s, 3H total), 2.45–2.75 (major and minor br s, 2H total), 2.85 (s, 1H), 2.99 (m, 3H), 3.05–3.2 (m, 2H), 3.23–3.75 (m, 7H), 3.78 (s, 3H), 4.90 (br q, 1H), 6.83 (d, 1H), 6.89 (t, 1H), 7.05–7.15 (m, 6H), 7.20 (br t, 1H), 7.25–7.30 (m, 5H).

EXAMPLE 3

(S)-2-(2-(1-Piperidinyl)ethylaminocarbonyl)-1-[N-(3-chlorophenyl)-N-phenylcarbamoyl]-4-(N,N-di-n-pentylcarbamoyl)piperazine According to the procedure of Example 1, Step E above, 40 mg (0.074 mmole) of 1-[N-(3-chlorophenyl)-N-phenylcarbamoyl]-4-(N,N-di-n-pentylcarbamoyl)-piperazine-2-carboxylic acid, 11 mg (0.081 mmole) of HOBt, 20 mg (0.103 mmole) of EDAC, and 19 mg (0.147 mmole) of 1-(2-aminoethyl)piperidine after purification by flash chromatography on 16 g of silica gel with 100:5:0.25 $CH_2Cl_2$:MeOH: ammonia water provided 44 mg (92%) of an oil.

Mass Spectrum (FAB): m/Z 653 (M+H, 100%), 230 (15%).

$^1$H NMR ($CDCl_3$, 400 MHz, ppm): δ 0.85 (t, 6H), 1.1–1.3 (m, 8H), 1.35–1.56 (m, 10H), 2.3–2.45 (m, 6H), 2.72 (td, 1H), 2.79 (br d, 1H), 3.0–3.4 (m, 8H), 3.75 (br d, 1H), 3.90 (d, 1H), 4.47 (br s, 1H), 6.95–7.06 (m, 3H), 7.07–7.15 (m, 3H), 7.15–7.25 (m, 2H), 7.3–7.4 (m 2H).

EXAMPLE 4

(S)-2-(2-(1-Piperidinyl)ethylaminocarbonyl)-4-(N,N-di-n-pentylcarbamoyl)-1-(N,N-diphenylcarbamoyl)piperazine According to the procedure of Example 1, Step E above, 53 mg (0.10 mmole) of 1-(N,N-diphenylcarbamoyl)-4-(N,N-di-n-pentylcarbamoyl)piperazine-2carboxylic acid, 16 mg (0.11 mmole) of HOBt, 28 mg (0.15 mmole) of EDAC, and 27 mg (0.21 mmole) of 1-(2-aminoethyl)piperidine after purification by flash chromatography on 16 g of silica gel with 100:5:0.25 $CH_2Cl_2$:MeOH: ammonia water provided 58 mg (89%) of an oil.

Mass Spectrum (FAB): m/Z 619 (M+H, 100%), 450 (7%), 196 (10%).

$^1$H NMR (CDCl$_3$, 400 MHz, ppm): δ 0.86 (t, 6H), 1.15–1.3 (m, 8H), 1.35–1.6 (m, 10H), 2.3–2.45 (m, 6H), 2.68 (td, 1H), 2.78 (dd, 1H), 3.0–3.3 (m, 7H), 3.35 (m, 1H), 3.78 (br d, 1H), 3.91 (d, 1H), 4.51 (br s, 1H), 6.93 (br s, 1H), 7.05–7.15 (m, 6H), 7.25–7.35 (m, 4H).

EXAMPLE 5

(S)-2-(2-(N,N-Bis(2-methoxybenzyl)amino)ethylaminocarbonyl)-1-(N,N-diphenyl carbamoyl)-4-(N,N-di-n-pentylcarbamoyl)piperazine A solution of 84 mg (0.15 mmole) of 1-(N,N-diphenylcarbamoyl)-4-(N,N-di-n-pentylcarbamoyl)-2-(2-aminoethylaminocarbonyl)piperazine, 22 mg (0.17 mmole) of DIEA and 48 mg (0.15 mmole) of 2-methoxybenzyl chloride (as a 50% solution in CHCl$_3$) in 1 mL of MeCN was stirred at 22° C. for 3 days. The volatiles were removed with a gentle stream of nitrogen and the residue was purified by flash chromatography on 23 g of silica gel eluting with 300 mL of 100:3:0.2 $CH_2Cl_2$:MeOH:ammonia water to give 42 mg (69%) of an oil.

Mass Spectrum (FAB): m/Z 792 (M+H, 40%), 270 (30%), 196 (15%), 121 (MeOPhCH$_2$, 100%).

$^1$H NMR (CDCl$_3$, 400 MHz, ppm): δ 0.82 (t, 6H), 1.1–1.3 (m, 8H), 2.35–2.45 (m, 4H), 2.57 (t, 2H), 2.65 (td, 1H), 2.80 (dd, 1H), 2.97–3.17 (m, 6H), 3.25 (m, 1H), 3.40 (m, 1H), 3.77 (s, 4H), 3.75 (m, 2H), 3.78 (s, 6H), 4.49 (br s, 1H), 6.63 (br t, 1H), 6.84 (d, 2H), 6.89 (t, 2H), 7.05 (d, 4H), 7.09 (t, 2H), 7.15–7.25 (m, 6H), 7.40 (d, 2H).

EXAMPLE 6

(S)-4-(N,N-Di-n-pentylcarbamoyl)-1-(N,N-diphenylcarbamoyl)-2-(2-(4-morpholinyl)ethylaminocarbonyl)-piperazine According to the procedure of Example 1, Step E above, 47 mg (0.09 mmole) of 1-(N,N-diphenylcarbamoyl)-4-(N,N-di-n-pentylcarbamoyl)piperazine-2-carboxylic acid, 3 mg (0.02 mmole) of DMAP, 25 mg (0.13 mmole) of EDAC, and 24 mg (0.18 mmole) of 4-(2-aminoethyl)morpholine after purification by flash chromatography on 16 g of silica gel with 100:3$CH_2Cl_2$:MeOH provided 26 mg (46%) of an oil.

Mass Spectrum (FAB): m/Z 621 (M+H, 100%), 255 (50%).

$^1$H NMR (CDCl$_3$, 400 MHz, ppm): δ 0.85 (t, 6H), 1.1–1.3 (m, 8H), 1.44 (quintet, 4H), 2.3–2.5 (m, 6H), 2.69 (td, 1H), 2.80 (dd, 1H), 32.0–3.4 (m, 8H), 3.66 (t, 4H), 3.72 (d, 1H), 3.91 (d, 1H), 4.48 (s, 1H), 7.0–7.4 (m, 11H).

EXAMPLE 7

(S)-2-(2-(N-Benzyl-N-methylamino)-N-(methyl)ethylaminocarbonyl)-4-(N,N-di-n-pentylcarbamoyl)-1-(N,N-diphenylcarbamoyl)piperazine According to the procedure of Example 1, Step E above, 48 mg (0.094 sole) of 1-(N,N-diphenylcarbamoyl)-4-(N,N-di-n-pentylcarbamoyl)piperazine-2carboxylic acid, 14 mg (0.104 mmole) of HOBt, 25 mg (0.132 mmole) of EDAC, and 34 mg (0.19 mmole) of N-benzyl-N-methyl-N'-methylethylenediamine after purification by flash chromatography on 16 g of silica gel eluting with 400 mL of 100:4 $CH_2Cl_2$:MeOH provided 49 mg (78%) of an oil.

Mass Spectrum (FAB): m/Z 669 (M+H, 100%), 306 (20%), 196 (Ph$_2$NCO, 80%).

$^1$H NMR (CDCl$_3$, 400 MHz, ppm): δ 0.85 (m, 1.1–1.3 (m, 8H), 1.35–1.5 (m, 4H), 2.03 (d, ~0.5H), 2.1–2.3 (m, 3.5H), 2.4–3.7 (several m, 18H), 4.85–4.95 (two overlapping t, total 1H), 7.0–7.35 (m, 15H).

EXAMPLE 8

(S)-1-(N-(3-Chlorophenyl)-N-phenylcarbamoyl)-2-(2-(N-methyl-N-(2-methoxybenzyl)amino)ethylaminocarbonyl)-4-(N,N-di-n-pentylcarbamoyl)piperazine

Step A:

N-(3-Chlorophenyl)-N-phenylcarbamoyl)piperazine

A solution of 20.4 g (100 mmole) of commercial 3-chlorodiphenylamine in 40 mL of toluene and 100 mL (193 mmole) of 1.93M phosgene in toluene were combined and heated at 90° C. under nitrogen for 2 hours with stirring. The red-orange solution was cooled, flushed with nitrogen for 2 hours to remove excess phosgene and concentrated in vacuo to provide 15.4 g (58%) of a red-orange oil which was homogeneous by TLC (4:1 hexanes-ethyl acetate), R$_f$=0.8).

Mass Spectrum (FAB): m/e 266 (M+1).

IR (neat, cm$^{-1}$): 1740, no NH absorption.

Step B:

(S)-1-[N-(3-Chlorophenyl-N-phenylcarbamoyl]-4-(benzyloxycarbonyl)piperazine-2-carboxylic acid A solution of 2.66 g (10 mmole) of N-(3-chlorophenyl)-N-phenylcarbamoyl chloride (from Step A) in 10 ml of chloroform was added dropwise to a stirring solution of 3.24 g (10 mmole) of (S)-4-(benzyloxycarbonyl)piperazine-2-carboxylic acid (from Example 7, Step A), 2.72 g (25 mmole) of chlorotrimethylsilane and 4.91 g (38 mmole) of N,N-diisopropylethylamine in 60 ml of chloroform at 10° C. The reaction mixture was allowed to warm to room temperature and stirring was continued for 60 hours. The reaction mixture was concentrated in vacuo and water and ether were added. The ethereal solution was extracted with 2N HCl and washed with water until neutral. The organic layer was then extracted with saturated sodium bicarbonate. A tan oil which separated was combined with the aqueous solution, and the mixture was acidified with 2N HCl. The resulting mixture was extracted with methylene chloride, and the organic extract was concentrated in vacuo to give 2.80 g (57%) of white solid, m.p. 100° C. (softened <80° C.); TLC: R$_f$0.60 [Analtech SGF plate developed with isoamyl alcohol-acetone-water (5:2:1)].

Mass spectrum (FAB): m/e 494 (M+1).

Analysis (C$_{26}$H$_{24}$N$_3$O$_5$Cl): Calculated: C, 63.22; H, 4.90; N, 8.51 Found: C, 62.98; H, 4,98; N, 8.34.

Step C:
(S)-1-[N-(3-Chlorophenyl)-N-phenylcarbamoyl]-piperazine-2-carboxylic acid hydrobromide 1.60 g (3.24 mmole) of (S)-1-[N-(3-chlorophenyl)-N-phenylcarbamoyl]-4-(benzyloxycarbonyl)piperazine-2-carboxylic acid (from Step B) was dissolved in 16 ml of 30% HBr in acetic acid. After stirring for 16 hours at 25° C., the solution was flushed with nitrogen to remove the excess of HBr. Next the solution was concentrated in vacuo and the residue was triturated with ether. The white solids which separated were recrystallized from methanol-ester to give 1.17 g (82%) of the product, mp 185° C. dec.

Mass spectrum (FAB): m/e 360 (M+1).

Analysis ($C_{18}H_{18}N_3O_3Cl \cdot HBr \cdot 1.5\ H_2O$): Calculated: C, 46.18; H, 4.70; N, 8.98 Found: C, 46.20; H, 4.35; N, 8.66.

Step D:
(S)-1-[N-(3-Chlorophenyl)-N-phenylcarbamoyl]-4-(dipentylcarbamoyl)piperazine-2-carboxylic acid To a suspension of 1.05 g (2.3 mmole) of (S)-1-[N-(3-chlorophenyl)-N-phenylcarbamoyl]piperazine-2carboxylic acid hydrobromide (from Step C) in 20 ml of methylene chloride was added 1.23 g (9.5 mmole) of N,N-diisopropylethylamine followed by the dropwise addition of a solution of 523 mg (2.38 mmole) of dipentylcarbamoyl chloride (from Example 1, Step C-2) in 5 ml of methylene chloride. After stirring 24 hours at 25° C., the solution was extracted with 2N HCl, then $H_2O$ and dried over $MgSO_4$. The dried methylene chloride solution was concentrated in vacuo and the residue was dissolved in isopropyl ether and was diluted with petroleum ether (bp. 30°–60° C.) until cloudy. The oil which precipitated was then decanted, redissolved in isopropanol and concentrated in vacuo to yield 464 mg (36%) of (S)-1-[N-(3-chlorophenyl)-N-phenylcarbamoyl]-4-(dipentylcarbamoyl)piperazine-2-carboxylic acid as a glassy solid; TLC showed a single spot, $R_f$ 0.75 (Analtech SGF plates developed with isoamyl alcohol-:acetone:water [5:2:1]).

Mass spectrum (FAB): m/e 542 (M+1).

Analysis ($C_{29}H_{39}N_4O_4Cl$) Calculated: C, 64.13; H, 7.24; N, 10.32 Found: C, 63.70; H, 6.85; N, 10.23.

$^1$H NMR (CDCl$_3$, 400 MHz, ppm): δ 0.85 (t, 6H), 1.19 (m, 4H), 1.27 (m, 4H), 1.45 (m, 4H), 2.68 (t of d, 1H), 2.91 (d of d, 1H), 3.11 (m, 4H), 3.19 (m, 1H), 3.28 (d, 1H), 3.62 (d, 1H), 3.92 (d, 1H), 4.74 (s, 1H), 6.99 (d, 1H), 7.06–7.13 (m, 4H), 7.19 (m, 2H), 7.33 (t, 2H).

Step E: Preparation of N-(2-Methoxybenzyl)-N-methylethylenediamine a) N-(2-Methoxybenzyl)-N-(methyl)aminoacetonitrile

A mixture of 2.0 g (13.2 mmole) of N-methyl-2-methoxybenzylamine, 0.99 g (13.2 mmole) of chloroacetonitrile, and 2.80 g (26.5 mmole) of powdered sodium carbonate was stirred in 30 mL of acetone at room temperature for 4 days. The mixture was concentrated in vacuo and the residue purified by flash chromatography on 130 g of silica gel eluting with 83:17 hexanes:ethyl acetate to give 2.2 g (87%) of an oil.

$^1$H NMR (CDCl$_3$, 400 MHz, ppm): δ 2.43 (s, 3H), 3.48 (s, 2H), 3.62 (s, 2H), 3.83 (s, 3H), 6.88 (d, 1H), 6.93 (t, 1H), 7.2–7.3 (m, 2H).

b) N-(2-Methoxybenzyl)-N-methylethylenediamine

To a stirred slurry of 0.56 g (15 mmole) of lithium aluminum hydride in 15 mL of diethyl ether under an atmosphere of nitrogen was added a solution of 2.2 g (11.6 mmole) of N-(2-methoxybenzyl)-N-(methyl)aminoacetonitrile in 20 mL of diethyl ether. The mixture was heated at reflux for 1 hour and then was allowed to cool to room temperature. The excess hydride was quenched cautiously with aqueous sodium hydroxide, and the resulting suspension was filtered through a pad of sodium sulfate, which was rinsed with additional diethyl ether. The filtrate was concentrated in vacuo to give 2.25 g (~100%) of a clear oil.

$^1$H NMR (CDCl$_3$, 200 MHz, ppm): δ 1.30 (br s, 2H), 2.20 (s, 3H), 2.46 (t, 2H), 2.80 (t, 2H), 3.49 (s, 2H), 3.79 (s, 3H), 6.8–6.95 (m, 2H), 7.15–7.35 (m, 2H).

Step F:
(S)-1-(N-(3-chlorophenyl)-N-phenylcarbamoyl)-2-(2-(N-methyl-N-(2-methoxybenzyl)amino)ethylaminocarbonyl)-4-(N,N-di-n-pentylcarbamoyl) piperazine According to the procedure of Example 1, Step E above, 43 mg (0.079 mmole) of (S)-4-(dipentylcarbamoyl)-1-(N-(3-chlorophenyl)-N-phenylcarbamoyl)-piperazine-2-carboxylic acid, 12 mg (0.087 mmole) of HOBt, 21 mg (0.111 mmole) of EDAC, and 31 mg (0.158 mmole) of N-(2-methoxybenzyl)-N-methylethylenediamine after purification by flash chromatography on 16 g of silica gel eluting with 100:4 CH$_2$Cl$_2$:methanol provided 48 mg (84%) of an oil.

Mass Spectrum (FAB): m/Z 720 (M+H, 85%), 517 (M-ClPhNPh, 5%), 230 (ClPhN(Ph)CO, 10%), 184 ([CH$_3$(CH$_2$)$_4$]$_2$NCO, 20%), 164 MePhCH$_2$N(CH$_3$)CH$_2$, 40%), 121 (MeOPhCH$_2$, 100%).

$^1$H NMR (CDCl$_3$, 400 MHz, ppm): δ 0.84 (t, 1.1–1.3 (m, 8H), 1.43 (quintet, 4H), 2.22 (br s, 3H), 2.52 (t, 2H), 2.68 (td, 1H), 2.81 (dd, 1H), 3.0–3.25 (m, 7H), 3.25–3.35 (m, 1H), 3.35–3.45 (m, 1H), 3.54 (br s, 2H), 3.72 (d, 1H), 3.79 (s, 3H), 3.89 (d, 1H), 4.49 (s, 1H), 6.88–6.9 (m, 2H), 6.9–7.05 (m, 2H), 7.05–7.35 (m, 9H).

EXAMPLE 9
(S)-4-(N,N-Di-n-pentylcarbamoyl)-1-(N-(3-chlorophenyl)-N-phenylcarbamoyl)-2-(2-(N-(2-methoxybenzyl)-N-(carbamoylmethyl)amino)-N-(methyl)ethylaminocarbonyl)piperazine

Step A: N-(t-Butoxycarbonyl)ethylenediamine

To a solution of 1.65 g (27.5 mmole) of ethylenediamine in 20 mL of CH$_2$Cl$_2$ was added a solution of 2.00 g (9.16 mmole) of di-t-butyl dicarbonate in 8 mL of CH$_2$Cl$_2$ dropwise over 20 min at room temperature. After 48 hours, the mixture was filtered and the filtrate concentrated in vacuo to give 1.4 g of an oil.

$^1$H NMR (CDCl$_3$, 200 MHz, ppm): 5 1.13 (br s, 2H), 1.42 (s, 9H), 2.77 (t, 2H), 3.15 (q, 2H), 4.85 (v br s, 1H).

Step B: N-(t-Butoxycarbonyl)-N'-(benzyloxycarbonyl)-N'-(carbamoylmethyl) ethylenediamine To a solution of 1.25 g (7.8 mmole) of N-(t-butoxycarbonyl)ethylenediamine in 10 mL of acetonitrile was added 1.36 mL (7.8 mole) of DIEA followed by 1.44 g (7.8 mmole) of iodoacetamide at room temperature. After 90 min most of the solvent was removed in vacuo and the residue was taken up in 12 mL of CH$_2$Cl$_2$ and was treated with 1.36 mL (7.8 mmole) of DIEA and then 1.1 mL (7.8 mmole) of benzyl chloroformate. The resulting solution was stirred at room temperature for 2 days, and was then concentrated partly in vacuo. The residue was treated with 100 mL of ethyl acetate and 20 mL of 1M aqueous tartaric acid and the layers were separated. The organic layer was washed with 2×15 mL of water, the tartaric acid layer was extracted with 30 mL of ethyl acetate, this extract was washed with 2×10 mL of water, and the combined organic layers were dried over sodium sulfate, filtered and concentrated in vacuo. The residue was purified by flash chromatography on 131 g of silica gel eluting with 2.5 L of 100:4 $CH_2Cl_2$:methanol to provide 1.5 g (55%) of an oil.

Mass Spectrum (FAB): m/Z 352 (M+H, 5%), 296 (M-isobutylene +H, 8%), 252 (M-isobutylene —$CO_2$+H, 100%).

$^1$H NMR ($CDCl_3$, 400 MHz, ppm): δ 1.40 (s, 9H), 3.29 (br s, 2H), 3.45 (t, 2H), 3.9 (s, 2H), 5.12 (s, 2H), 5.1–5.3 (br d, 1H), 5.59 (br s, 1H), 6.1–6.35 (br m, 1H), 7.25–7.35 (br m, 5H).

Step C:
N-(Benzyloxycarbonyl)-N-(carbamoylmethyl)ethylenediamine trifluoroacetic acid salt A mixture of 0.16 g (0.46 mmole) of N-(t-butoxycarbonyl)-N'-(benzyloxycarbonyl)-N'-(carbamoylmethyl) ethylenediamine and 0.4 mL of anisole was treated at 0° C. with 2 mL of ice cold trifluoroacetic acid under nitrogen. After 90 min at 0° C., the solution was concentrated in vacuo employing a high vacuum pump and with the heating bath at 48° C. for several hours. The resulting oil was employed directly in Step D below.

Step D:
(S)-2-(2-(N-(Benzyloxycarbonyl)-N-(methylcarboxamido)amino)ethylaminocarbonyl)-4-(N,N-di-n-pentylcarbamoyl)-1-(N-(3-chlorophenyl)-N-phenylcarbamoyl)piperazine According to the procedure of Example 1 Step E above, 77 mg (0.14 mmole) of (S)-4-(dipentylcarbamoyl)-1-(N-(3-chlorophenyl)-N-phenylcarbamoyl)-piperazine-2-carboxylic acid, 21 mg (0.16 mmole) of HOBt, 38 mg (0.20 mmole) of EDAC, 83 mg (ca. 0.23 mmole) of N-(benzyloxycarbonyl)-N-(carbamoylmethyl)ethylenediamine trifluoroacetic acid salt and 31 microliters (0.23 mmole) of triethylamine after purification by flash chromatography on 23 g of silica gel eluting with 450 mL of 100:3 $CH_2Cl_2$:methanol, then 100 mL of 100:4 $CH_2Cl_2$:methanol, then 100 mL of 100:5 $CH_2Cl_2$:methanol gave 100 mg (90%) of an oil.

Mass Spectrum (FAB): m/Z 799 (M+Na, 18%), 777 (M+H, 90%), 574 (15%), 230 (ClPhN(Ph)CO, 55%), 184 ([$CH_3(CH_2)_4$]$_2$NCO, 100%), 167 (40%).

$^1$H NMR ($CDCl_3$, 400 MHz, ppm): δ 0.85 (t, 6H), 1.1–1.3, 8H), 1.45 (quintet, 4H), 2.69 (br t, 1H), 2.91 (dd, 1H), 3.0–3.2 (m, 5H), 3.2–3.6 (m, 5H), 3.7–4.0 (m, 3H), 4.40 (br s, 1H), 5.0–5.15 (m, 2H), 5.47 (br s, 1H), 6.3 and 6.7 (minor and major br s, 1H), 6.99 (d, 1H), 7.05–7.4 (m, 14H), 7.75 (br s, 1H).

Step E:
(S)-1-(N-(3-Chlorophenyl)-N-phenylcarbamoyl)-2-(2-(N-(carbamoylmethyl)amino)ethylaminocarbonyl)-4-(N,N-di-n-pentylcarbamoyl)piperazine A solution of 89 mg (0.11 mmole) of 2-(2-(N-(benzyloxycarbonyl)-N-(carbamoylmethyl)amino)-N-(methyl)ethylaminocarbonyl)-4-(N,N-di-n-pentylcarbamoyl)-1-(N-(3-chlorophenyl)-N-phenylcarbamoyl)-piperazine in 6 mL of ethanol was treated with 50 mg of 10% Pd/C, and the resulting suspension was stirred under an atmosphere of hydrogen for 25 min. The mixture was then filtered through Celite and the filtrate concentrated in vacuo. The residue was carried on in Step F below.

Step F:
(S)-4-(N,N-Di-n-pentylcarbamoyl)-1-(N-(3-chlorophenyl)-N-phenylcarbamoyl)-2-(2-(N-(2-methoxybenzyl)-N-(carbamoylmethyl)amino)ethylaminocarbonyl)piperazine A solution of 74 mg (ca. 0.11 mmole) of 1-(N-(3-chlorophenyl)-N-phenylcarbamoyl)-2-(2-(N-(methylcarboxamido)amino)-N-(methyl)ethylaminocarbonyl)-4-(N,N-di-n-pentylcarbamoyl)piperazine (from Step E above) in 2 mL of acetonitrile was treated with 72 mg (0.23 mmole) of a 50 wt % solution of 2-methoxybenzyl chloride in chloroform and 60 microliters (0.35 mmole) of DIEA, and the mixture was stirred at room temperature for 24 hours and then at 80° C. for 36 hours. After cooling to room temperature, the mixture was concentrated in vacuo and the residue purified by flash chromatography on 23 g of silica gel eluting with 500 mL of 100:3:0.1 $CH_2Cl_2$:methanol:ammonia water. Impure fractions containing product were resubmitted to the chromatographic conditions given above. The pooled product fractions were then purified by flash chromatography on 23 g of silica gel eluting with 700 mL of 100:2 $CH_2Cl_2$:methanol and then 200 mL of 100:4 $CH_2Cl_2$:methanol to provide 20 mg (23%) of an oil.

Mass Spectrum (FAB): m/Z 763 (M+H, 35%), 230 (ClPhN(Ph)CO, 55%), 207 (40%), 184 ([$CH_3(CH_2)_4$]$_2$NCO, 100%).

$^1$H NMR ($CDCl_3$, 400 MHz, ppm): δ 0.85 (t, 6H), 1.1–1.3 (m, 8H), 1.43 (quintet, 4H), 2.58 (t, 2H), 2.75 (td, 2H), 2.85–3.05 (m, 4H), 3.05–3.3 (m, 6H), 3.6–3.7 (3H), 3.79 (s, 3H), 3,83 (d, 1H), 4.3 (s, 1H), 5.23 (d, 1H), 6.8–6.9 (m, 2H), 7.0–7.15 (m, 5H), 7.15–7.25 (m 4H), 7.33 (app t, 2H), 7.52 (br s, 2H).

EXAMPLE 10

(S)-1-(N-(3,5-Dimethylphenyl)-N-phenylcarbamoyl)-2-(2-(N-methyl-N-(2-methoxybenzyl)amino)ethylaminocarbonyl)-4-(N,N-di-n-pentylcarbamoyl)piperazine step A: N-acetyl-3,5-dimethylaniline To a solution of 15.2 g (125 mmole) of 3,5-dimethylaniline in 60 mL of toluene was added 15 g (146 mmole) of acetic anhydride, whereupon the internal temperature rose to 75° C. The mixture was allowed to cool to room temperature and the solvent was removed in vacuo. The residue was dissolved in 150 mL of hot ethyl acetate and the solution allowed to stand for 16 hours. The resulting mixture was cooled at 5° C. for 3 hours and the solid collected by filtration to give 18.43 g (90%) of off-white crystals.

$^1$H NMR ($CDCl_3$, 400 MHz, ppm): δ 2.14 (s, 3H), 2.29 (s, 6H), 6.73 (s, 1H), 7.05 (br s, 1H), 7.11 (s, 2H).

Step B: N-(3,5-Dimethylphenyl)aniline

A mixture of 9.6 g (58.8 mmole) of N-acetyl-3,5-dimethylaniline, 8.13 g (58.8 mmole) of potassium carbonate (dried at 155° C. under vacuum), 23 g (147 mmole) of bromobenzene (dried over molecular sieves), and 1.12 g (5.9 mmole) of cuprous iodide was heated in a 175° C. oil bath under a reflux condenser under nitrogen for 18 hours. The mixture was cooled to room temperature and triturated with 1 liter of benzene. The solution was concentrated in vacuo. The residue was treated with 60 mL of EtOH and 7.76 g (118 mmole) of potassium hydroxide and the resulting mixture was heated to reflux for two hours. The mixture was cooled and the solvent removed in vacuo. The residue was taken up in 150 mL of hexanes and 20 mL of EtOAc and the resulting solution was washed with 2×100 mL of 2N aqueous HCl and 60 mL of water. The organic layer was dried over sodium sulfate, filtered and concentrated in vacuo. The residue was purified by flash chromatography on 210 g of silica gel with 2 liters of 3:1 hexanes $CH_2Cl_2$ to give 5.5 g (47%) of a light red oil.

$^1$H NMR ($CDCl_3$, 400 MHz, ppm): δ 2.24 (s, 6H), 5.60 (br s, 1H), 5.59 (s, 1H), 6.71 (s, 2H), 6.91 (t, 1H), 7.05 (d, 2H), 7.2–7.3 (m, 2H).

Step C: N-(3,5-Dimethylphenyl)-N-phenylcarbamoyl chloride

A solution of 5.5 g (27.9 mmole) of N-(3,5-dimethylphenyl)aniline, 27.9 mL of 1.93M phosgene in toluene and 15 mL of toluene was heated at 90° C. under nitrogen for 2 hours with stirring. The solution was cooled, flushed with nitrogen for 2 hours to remove excess phosgene and concentrated in vacuo to give 7.15 g (99%) of a red oil.

NMR ($CDCl_3$, 400 MHz, ppm): δ 2.29 (s, 6H), 6.92 (br s, 3H), 7.2–7.45 (m, 5H).

Step D:
(S)-4-(Benzyloxycarbonyl)-1-[N-(3,5-dimethylphenyl)-N-phenylcarbamoyl]-piperazine-2-carboxylic acid A mixture of 800 mg (2.72 mmole) of (S)-4-(benzyloxycarbonyl)piperazine-2-carboxylic acid, 707 mg (2.72 mmole) of N-(3,5-dimethylphenyl)-N-phenylcarbamoyl chloride and 760 mg (5.45 mmole) of triethylamine was stirred in 10 mL of DMF for 48 hours at room temperature. The solution was concentrated in vacuo and the residue purified by flash chromatography on 125 g of silica gel eluting with 1 liter of 100:2 $CH_2Cl_2$:MeOH then 800 mL of 100:5:0.2 $CH_2Cl_2$:MeOH:HOAc to give 1.32 g of an oil which by 1H NMR contained residual DMF and HOAc.

Step E:
(S)-1-[N-(3,5-Dimethylphenyl)-N-phenylcarbamoyl]-piperazine-2-(S)-carboxylic acid acetate salt A solution of (S)-1-[N-(3,5-dimethylphenyl)-N-phenylcarbamoyl]-4-(benzyloxycarbonyl)piperazine-2-(S)-carboxylic acid (prepared in Step D above) in 9 mL of MeOH was treated with 7 drops of acetic acid and 170 mg of 10% Pd/C. The mixture was stirred under an atmosphere of hydrogen for 4 hours, when an additional 50 mg of 10% Pd/C was added. After stirring under an atmosphere of hydrogen for an additional 2 hours, the mixture was filtered through Celite and the filter cake rinsed with 200 mL of MeOH. The filtrate was concentrated in vacuo to give 228 mg of a white paste which was carried on in Step F below.

Step F:
(S)-1-[N-(3,5-Dimethylphenyl)-N-phenylcarbamoyl]-4-(N,N-di-n-pentylcarbamoyl)piperazine-2-carboxylic acid A mixture of 220 mg (0.53 mmole) of 1-[N-(3,5-dimethylphenyl)-N-phenylcarbamoyl]piperazine-2-(S)-carboxylic acid acetate salt (from Step E above), 175 mg (0.80 mmole) of N,N-di-n-pentylcarbamoyl chloride (from Example 1, Step C-2) and 188 mg (1.86 mmole) of triethylamine in 6 mL of THF and 3 mL of water was stirred at 55° C. for 72 hours. To the mixture was added an additional 6 mL of THF, 175 mg of N,N-di-n-pentylcarbamoyl chloride, and 187 mg of triethylamine and the mixture again heated at 55° C. for 48 hours. To the mixture was added an additional 120 mg N,N-di-n-pentylcarbamoyl chloride and the reaction mixture heated for an additional 24 hours. The mixture was cooled and was partitioned between 16 mL of 0.5N aqueous HCl and 30 mL of EtOAc. The layers were separated and the aqueous layer extracted with 2×40 mL of EtOAc. The organic layer was dried over magnesium sulfate, filtered and concentrated in vacuo. The residue was purified by flash chromatography on 68 g of silica gel eluting with 100:4:0.1 $CH_2Cl_2$:MeOH:HOAc to give 194 mg (68%) of an oil.

Mass Spectrum (FAB): m/Z 559 (M+Na, 4%), 537 (M+H) 60%), 532 (20%), 492 (M—$CO_2$H, 5%), 341 (M-PhNAr, 15%), 308 (20%), 224 (ArN(CO)Ph, 95%), 196 (45%), 184 ([$CH_3(CH_2)_4]_2$NCO, 100%).

$^1$H NMR ($CDCl_3$, 400 MHz, ppm): δ 0.85 (t, 6H), 1.1–1.35 (m, 8H), 1,45 (quintet, 4H), 2.24 (s, 6H), 2.64 (t, 1H), 2.90 (d, 1H), 3.05–3.25 (m, 6H), 3.61 (d, 1H), 3.93 (d, 1H), 4.74 (s, 1H), 6.72 (s, 2H), 6.79 (s, 1H), 7.05–7.15 (m, 3H), 7.29 (t, 2H).

Step G:
(S)-1-(N-(3,5-Dimethylphenyl)-N-phenylcarbamoyl)-2-(2-(N-methyl-N-(2-methoxybenzyl)amino)ethylaminocarbonyl)-4-(N,N-di-n-pentylcarbamoyl) piperazine According to the procedure of Example 1, Step E above, 41 mg (0.076 mmole) of (S)-1-[N-(3,5-dimethylphenyl)-N-phenylcarbamoyl]-4-(N,N-di-n-pentylcarbamoyl)piperazine-2-carboxylic acid, 11 mg (0.084 mmole) of HOBt, 21 mg (0.111 mmole) of EDAC, and 30 mg (0.153 mmole) of N-(2-methoxybenzyl)-N-methylethylenediamine (from Example 1, Step E b) above) after purification by flash chromatography on 16 g of silica gel eluting with 100:4:0.2 $CH_2Cl_2$:methanol:ammonia water provided 41 mg (75%) of an oil.

Mass Spectrum (FAB): m/Z 714 (~M+H, 70%), 224 (ArN(Ph)CO, 35%), 184 ([$CH_3(CH_2)_4]_2$NCO, 35%), 121 (MeOPhCH$_2$, 100%).

$^1$H NMR ($CDCl_3$, 400 MHz, ppm): δ 0.84 (t, 6H), 1.1–1.3 (m, 8H), 1.4–1.5 (br quintet, 4H), 2.21 (s, H), 2.51 (br t, 2H), 2.64 (td, 1H), 2.78 (dd, 1H), 3.0–3.1 (m, 2H), 3.2–3.2 (m, 2H), 3.23–3.35 (m, 1H), 3.35–3.45 (m, 1H), 3.54 (s, 2H), 3.74 (d, 1H), 3.79 (s, 3H), 3.91 (d, 1H), 4.53 (s, 1H), 6.68 (s, 2H), 6.77 (s, 1H), 6.8–6.9 (m, 3H), 7.04–7.11 (m, 3H), 7.17–7.28 (m, 4H).

EXAMPLE 11

(S)-1-(N-(B,5-Dichlorophenyl)-N-phenylcarbamoyl)-2-(2-(N-methyl-N-(2-methoxybenzyl)amino)ethylaminocarbonyl)-4-(N,N-di-n-pentylcarbamoyl)piperazine

Step A: N-Acetyl-3,5-dichloroaniline

To a solution of 20 g (123 mmole) of 3,5-dichloroaniline in 80 mL of toluene was added 18.9 g (185 mmole) of acetic anhydride, whereupon the internal temperature rose to 75° C. The mixture was allowed to cool to room temperature and the solvent was removed in vacuo. The residue was dissolved in 150 mL of hot ethyl acetate and the solution allowed to stand for 16 hours. The resulting mixture was cooled at 5° C. for 3 hours and the solid collected by filtration to give 23g (91%) of off-white crystals.

¹H NMR (CDCl₃, 400 MHz, ppm): δ 2.17 (s, 3H), 7.08 (s, 1H), 7.25 (br s, 1H), 7.45 (s, 2H).

Step B: N-(3,5-Dichlorophenyl)aniline

A mixture of 12 g (58.8 mmole) of N-acetyl-3,5-dichloroaniline, 8.13 g (58.8 mmole) of potassium carbonate (dried at 155° C. under vacuum), 23 g (147 mmole) of bromobenzene (dried over molecular sieves), and 1.12 g (5.9 mmole) of cuprous iodide was heated in a 175° C. oil bath under a reflux condenser under nitrogen for 18 hours. The mixture was cooled to room temperature and triturated with 1 liter of benzene. The solution was concentrated in vacuo. The residue was treated with 50 mL of EtOH and 7.76 g (118 mmole) of potassium hydroxide and the resulting mixture was heated to reflux for two hours. The mixture was cooled and the solvent removed in vacuo. The residue was taken up in 150 mL of hexanes and 20 mL of EtOAc and the resulting solution was washed with 2×100 mL of 2N aqueous HCl and 70 mL of water. The latter wash was back extracted with 60 mL of ethyl acetate and the combined organic layers were dried over sodium sulfate, filtered and concentrated in vacuo. The residue was purified by flash chromatography on 200 g of silica gel with 2 liters of 50:1 hexanes:ethyl acetate to give 10 g (71%) of a yellow oil.

¹H NMR (CDCl₃, 400 MHz, ppm): δ 5.72 (br s, 1H), 6.83 (s, 1H), 6.85 (s, 2H), 7.0–7.1 (m, 3H), 7.28–7.35 (m, 2H).

Step C: N-(3,5-Dichlorophenyl)-N-phenylcarbamoylchloride

According to the procedure of Example 10, Step C, 10g (27.9 mmole) of N-(3,5-dichlorophenyl)aniline, 42 mL of 1.93M phosgene in toluene and 25 mL of toluene at a bath temperature of 105° C. for 4.5 hr gave 10.98 g of a yellow oil, which by ¹H NMR was 40 mol % (46 wt %) product, the remainder being starting material.

Step D: (S)-4-(Benzyloxycarbonyl)-1-[N-(3,5-dichlorophenyl)-N-phenylcarbamoyl]piperazine-2-carboxylic acid A mixture of 900 mg (3.41 mmole) of (S)-4-(benzyloxycarbonyl)piperazine-2-carboxylic acid, 2.23 g (2.72 mmole of the carbamoyl chloride; remaining material is N-(3,5-dichlorophenyl)aniline from Step C) of N-(3,5-dichlorophenyl)-N-phenylcarbamoyl chloride and 689 mg (6.81 mmole) of triethylamine was stirred in 12 mL of DMF for 57 hours at room temperature. The solution was concentrated in vacuo and the residue taken up in 70 mL of ethyl acetate. This layer was washed with 15 mL of 0.5N aqueous hydrochloric acid and 2×20 mL of water, and the organic phase was dried over sodium sulfate, filtered and concentrated in vacuo. The residue was purified by flash chromatography on 195 g of silica gel eluting with 2.8 L of 100:3:0.2 CH₂Cl₂:MeOH:-HOAc to give 1.2 g of an oil which by ¹H NMR contained residual DMF and HOAc.

Mass Spectrum (FAB): m/Z 529 (M+H, 60%), 266 (Cl₂PhN(Ph)CO, 75%), 264 (Cl₂PhN(Ph)CO, 100%), 237 (Cl₂PhNPh, 95%), 200 (ClPhNPh, 90%).

¹H NMR (CDCl₃, 400 MHz, ppm): δ 2.7 (br s, 1H), 3.04 (br d, 1H), 3.1–3.2 (m, 1H), 3.59 (br d, 1H), 3.89 (br s, 1H), 4.58 (d, 1H), 4.82 (br s, 1H), 5.05–5.2 (m, 2H), 6.94 (s, 2H), 7.11 (app d, 3H), 7.2–7.4 (m, 8H).

Step E: (S)-1-[N-(3,5-Dichlorophenyl)-N-phenylcarbamoyl]-piperazine-2-carboxylic acid A mixture of 0.63 g (1.19 mmole) of (S)-4-(benzyloxycarbonyl)-1-[N-(3,5-dichlorophenyl)-N-phenylcarbamoyl]piperazine-2-carboxylic acid and 12 mL of 30% HBr/acetic acid was stirred at room temperature for 40 min, and residual HBr was then removed by bubbling nitrogen through the solution for 3 hr. The mixture was then concentrated in vacuo. The residue was treated with 25 mL of water and the pH adjusted to 7 with aqueous sodium hydroxide. To this mixture was added 45 mL of ethyl acetate, and the ethyl acetate layer was extracted with 5×25 mL of water. The combined water layers were treated with aqueous sodium hydroxide to adjust the pH to 7, and the aqueous was concentrated in vacuo to give 0.73 g of an oily solid, which was carried on immediately in Step F) below.

Step F: (S)-1-[N-(3,5-Dichlorophenyl)-N-phenylcarbamoyl]-4-(N,N-di-n-pentylcarbamoyl)piperazine-2-carboxylic acid A mixture of 470 mg (1.19 mmole) of (S)-1-[N-(3,5-dichlorophenyl)-N-phenylcarbamoyl]piperazine-2-carboxylic acid (from Step E above), 393 mg (1.79 mmole) of N,N-di-n-pentylcarbamoyl chloride (from Example 1, Step C-2) and 578 mg (4.17 mmole) of triethylamine in 15 mL of THF and 8 mL of water was stirred at 55° C. for 24 hours. The mixture was cooled and treated with 16 mL of 0.5N aqueous hydrochloric acid, and the aqueous layer was extracted with 3×55 mL of ethyl acetate. The combined organic extracts piperazine-2-carboxylic acid (from Step E above), 393 mg (1.79 mmole) of N,N-di-n-pentylcarbamoyl chloride (from Example 1, Step C-2) and 578 mg (4.17 mmole) of triethylamine in 15 mL of THF and 8 mL of water was stirred at 55° C. for 24 hours. The mixture was cooled and treated with 16 mL of 0.5N aqueous hydrochloric acid, and the aqueous layer was extracted with 3×55 mL of ethyl acetate. The combined organic extracts were dried over sodium sulfate, filtered, and concentrated in vacuo. The residue was purified by flash chromatography on 120 g of silica eluting with 1 L of 100:3 methylene chloride:methanol then 1 L of 100:4.5:0.15 methylene chloride:methanol: acetic acid to give 374 mg (54%) of an oil.

Mass Spectrum (FAB): m/Z 1193 (2M+K, 20%), 571.

(M—CO₂H+K, 80%), 370 (55%), 151 (100%), ¹H NMR (CDCl₃, 400 MHz, ppm): δ (all peaks broad) 0.84 (t, 6H), 1.1–1.3 (m, 8H), 1.35–1.5 (m, 4H), 2.6–3.4 (m, 6H), 6.9–7.4 (m, 8H).

Step G: (S)-1-(N-(3,5-Dichlorophenyl)-N-phenylcarbamoyl)-2-(2-(N-methyl-N-(2-methoxybenzyl)amino)ethylaminocarbonyl)-4-(N,N-di-n-pentylcarbamoyl)piperazine According to the procedure of Example 1, Step E above, 46 mg (0.080 mmole) of (S)-1-[N-(3,5-dichlorophenyl)-N-phenylcarbamoyl]-4-(N,N-di-n-pentylcarbamoyl)piperazine-2-carboxylic acid, 12 mg (0.088 mole) of HOBt, 21 mg (0.112 mmole) of EDAC, and 31 mg (0.16 mmole) of N-(2-methoxybenzyl)-N-methylethylenediamine (from Example 1, Step E b) above) after purification by flash chromatography on 16 g of silica gel eluting with 100:5:CH₂Cl₂:methanol: provided 54 mg (90%) of an oil.

Mass Spectrum (FAB): m/Z 754 (M+H, 45%), 121 (MeOPhCH₂, 100%).

¹H NMR (CDCl₃, 400 MHz, ppm): δ 0.84 (t, 6H), 1.1–1.3 (m, 8H), 1.44 (quintet, 4H), 2.23 (br s, 3H), 2.52 (br s, 2H), 2.70 (t, 1H), 2.83 (br d, 1H), 3.0–3.45 (m, 8H), 3.56 (br s, 2H), 3.69 (br d, 1H), 3.80 (s, 3H), 3.87 (br d, 1H), 4.47 (s, 1H), 6.8–7.05 (m, 5H), 7.07 (m, 1H), 7.12 (d, 2H), 7.18–7.36 (m, 5H).

EXAMPLE 12

(S)-4-(N,N-Di-n-pentylcarbamoyl)-1-(N-(3,5-dichlorophenyl)-N-phenylcarbamoyl)-2-(2-N-(carbamoylmethyl)amino)ethylaminocarbonyl)piperazine Step A:
(S)-2-(2-(N-(Benzyloxycarbonyl)-N-(carbamoylmethyl)amino)ethylamino
carbonyl)-4-(N,N-di-n-pentylcarbamoyl)-1-(N-(3,5-dichlorophenyl)-N-phenylcarbamoyl)piperazine According to the procedure of Example 1, Step E above, 82 mg (0.14 mmole) of (S)-4-(dipentyl-carbamoyl)-1-(N-(3,5-dichlorophenyl)-N-phenylcarbamoyl)piperazine-2-carboxylic acid, 21 mg (0.16 mmole) of HOBt, 38 mg (0.20 mmole) of EDAC, 83 mg (ca. 0.23 mmole) of N-(benzyloxycarbonyl)-N-(carbamoylmethyl)ethylenediamine trifluoroacetic acid salt and 31 microliters (0.23 mmole) of triethylamine after purification by flash chromatography on 23 g of silica gel eluting with 700 mL of 100:3 CH₂Cl₂:methanol gave 95 mg (82%) of an oil, which contained minor impurities by TLC, This material was carried on immediately in Step B below.

Step B:
(S)-4-(N,N-Di-n-pentylcarbamoyl)-1-(N-(3,5-dichlorophenyl)-N-phenylcarbamoyl)-2-(2-N-(carbamoylmethyl)amino)ethylaminocarbonyl)piperazine A mixture of 95 mg (0.12 mmole) of 2-(2(N-(benzyloxycarbonyl)-N-(carbamoylmethyl)amino)ethylaminocarbonyl)-4-(N,N-di-n-pentylcarbamoyl)-1-N-(3,5-dichlorophenyl)-N-phenylcarbamoyl)piperazine (from Step A above) and 5 mL of 30% hydrobromic acid/acetic acid was stirred at room temperature for 20 min, and the excess hydrobromic acid was then removed by bubbling nitrogen through the solution for 1.5 hr, The solution was concentrated partly in vacuo and the residue was purified by flash chromatography on 16 g of silica eluting with 450 mL of 100:6:0,2 methylene chloride: methanol: ammonia water to give 57 mg (72%) of an oil, Mass Spectrum (FAB): m/Z 678,676 (M+H, 40%, 30%), 264 (ClPhN(Ph)CO, 30%), 200 (25%), 184 ([CH₃(CH₂)₄]₂NCO, 100%).

¹H NMR (CDCl₃, 400 MHz, ppm): δ 0.84 (t, 6H), 1.1–1.3 (m, 8H), 1.45 (quintet, 4H), 2.7–2.88 (m, 4H), 2.9–3.05 (m, 3H), 3.09–3.17 (m, 2H), 3.27 (s, 2H), 3.28–3.45 (m, 3H), 3.66 (d, 1H), 3.97 (d, 1H), 4.47 (s, 1H), 5.37 (s, 1H), 7.00 (m, 2H), 7.08 (m, 1H), 7.16 (d, 2H), 7.2–7.3 (m, 2H), 7.34–7.40 (m, 2H), 7.92 (br s, 1H).

EXAMPLE 13

(S)-4-(N,N-Di-n-pentylcarbamoyl)-1-(N-(3,5-dichlorophenyl)-N-phenylcarbamoyl)-2-(2-(N-(2-methoxybenzyl)N-(carbamolymethyl)amino)ethylaminocarbonyl)piperazine A solution of 30 mg (0.044 mmole) of 4-(N,N-di-n-pentylcarbamoyl)-1-(N-(3,5-dichlorophenyl)-N-phenylcarbamoyl)-2-(2-N-(carbamoylmethyl)amino)ethylaminocarbonyl)piperazine, 28 mg (0.089 mmole) of a 50 wt % solution of 2-methoxybenzyl chloride in chloroform and 0.016 mL (0.08g mmole) of DIEA in 3 mL of acetonitrile was heated in an 80° C. oil bath for 36 hr. The cooled mixture was concentrated in vacuo and the residue was purified by flash chromatography on 6 g of silica eluting with 450 mL of 100:2.75 methylene chloride:methanol to give 31 mg (89%) of an oil.

Mass Spectrum (FAB): m/Z 797 (M+H, 75%), 264 (Cl₂PhN(Ph)CO, 30%), 207 (MeOPhCH₂N(CH₂)CH₂CONH₂, 50%), 184 ([CH₃(CH₂)₄]₂NCO, 100%).

¹H NMR (CDCl₃, 400 MHz, ppm): δ 0.85 (t, 6H), 1.1–1.3 (m, 8H), 1.44 (quintet, 4H), 2.58 (t, 2H), 2.72 (dd, 1H), 2.75–3.35 (m, 9H), 3.27 (d, 1H), 3.4–3.5 (m, 1H) , 3.6–3.7 (m, 3H ), 3.89 (s, 3H), 3.93 (d, 1H), 4.28 ( s, 1H), 5.31 (br d, 1H), 6.82–6.87 (m, 2H), 6.99 (d, 2H), 7.09 (t, 1H) , 7.14 (app d, 2H), 7.2–7.25 (m, 3H), 7.34–7.38 (m, 3H), 7.55 (br d, 1H), 7.67 (br s, 1H).

EXAMPLE 14

(S)-4-(N,N-Di-n-pentylcarbamoyl)-1-(N,N-diphenylcarbamoyl)-2-(2-N-(carbamoylmethyl)amino)ethylaminocarbonyl)piperazine Step A:
(S)-2-(2-(N-(Benzyloxycarbonyl)-N-(carbamoylmethyl)amino)ethylamino
carbonyl)-4-(N,N-di-n-pentylcarbamoyl)-1-(N,N-diphenylcarbamoyl)piperazine According to the procedure of Example 1, Step E above, 60 mg (0.12 mmole) of (S)-4-(dipentylcarbamoyl)-1-(N,N-diphenylcarbamoyl)piperazine-2carboxylic acid, 18 mg (0.13 mmole) of HOBt, 32 mg (0.17 mmole) of EDAC, 86 mg (ca. 0.24 mmole) of N-(benzyloxycarbonyl)-N-(carbamoylmethyl)ethylenediamine trifluoroacetic acid salt and 33 microliters (0.24 mmole) of triethylamine after purification by flash chromatography on 16 g of silica gel eluting with 450 mL of 100:3.5 CH₂Cl₂:methanol followed by flash chromatography on 16 g of silica with 450 mL of 100:3 CH₂Cl₂:methanol then 200 mL of 100:5 CH₂Cl₂:methanol gave 62 mg (70%) of an oil.

Mass Spectrum (FAB): m/Z 743 (M+H, 80%), 573 (15%), 492 (15%), 464 (12%), 305 (12%), 278 (15%), 183 (100%), 167 (60%).

¹H NMR (CDCl₃, 400 MHz, ppm): 6 0.86 (t, 6H), 1.1–1.3 (m, 8H), 1.45 (quintet, 4H), 2.6–2.75 (m, 1H), 2.95 (br d, 1H), 3.0–3.6 (m, 12H), 3.75–4.0 (m, 4H), 4.42 (br s, 1H), 5.0–5.3 (m, 3H), 6.32, 6.64, ( br s, total 1H), 7.07–7.16 (m, 5H), 7.25–7.4 (m, 9H), 7.47 (m, 1H).

Step B:
(S)-4-(N,N-Di-n-pentylcarbamoyl)-1-(N,N-diphenylcarbamoyl)-2-(2-N-(methylcarboxamido)amino)ethylamino-carbonyl)piperazine A solution of 62 mg (0.084 mmole) of (S)-2-(2-(N-(benzyloxycarbonyl)-N-(carbamoylmethyl)amino)ethylamino carbonyl)-4-(N,N-di-n-pentylcarbamoyl)-1-

(N,N-diphenylcarbamoyl)piperazine in 6 mL of ethanol was treated with 35 mg of 10% Pd/C and was stirred under one atmosphere of hydrogen for 2 hr. The mixture was filtered through Celite, concentrated in vacuo, and the residue purified by flash chromatography on 16 g of silica eluting with 450 mL of 100:5:0.2 CH$_2$Cl$_2$:methanol:ammonia water to give 39 mg (76%) of an oil.

Mass Spectrum (FAB): m/Z 630 (M+Na, 8%), 608 (M+H, 35%), 195 (100%), 183 (80%), 167 (60%).

$^1$H NMR (CDCl$_3$, 400 MHz, ppm): δ 0.85 (t, 6H), 1.1–1.3 (m, 8H), 1.45 (quintet, 4H), 2.7–2.78 (m, 3H), 2.83 (dd, 1H), 2.98–3.05 (m, 3H), 3.1–3.2 (m, 2H), 3.2–3.27 (m, 1H), 3.27 (s, 3H), 3.28–3.43 (m, 2H), 3.65 (d, 1H), 3.94 (d, 1H), 4.41 (s, 1H), 5.14 (br s, 1H), 7.1–7.2 (m, 6H), 7.28–7.35 (m, 5H), 7.63 (br t, 1H).

EXAMPLE 15

(S)-4-(N,N-Di-n-pentylcarbamoyl)-1-(N,N-diphenylcarbamoyl)-2-(2-(N-(2-methoxybenzyl)-N-(carbamoylmethyl)amino)ethylaminocarbonyl)piperazine A solution of 23 mg (0.038 mmole) of (S)-4-(N,N-di-n-pentylcarbamoyl)-1-(N,N-diphenylcarbamoyl)-2-(2-N-(carbamoylmethyl)amino)ethylaminocarbonyl)piperazine, 0.007 mL (0.038 mmole) of DIEA, and 12 mg (0.038 mmole) of a 50 wt % solution of 2-methoxybenzyl chloride in chloroform in 1 mL of acetonitrile was stirred at room temperature for 9 days, at which time 6 mg more of the 2-methoxybenzyl chloride solution and 0.005 mL more DIEA was added. After 3 days more the mixture was concentrated with a stream of nitrogen and the residue purified by flash chromatography on 16 g of silica eluting with 400 mL of 100:4.5 CH$_2$Cl$_2$:methanol to give 20 mg (73%) of an oil.

Mass Spectrum (FAB): m/Z 729 (M+H,55%), 196 (Ph$_2$NCO, 28%), 184 ([CH$_3$(CH$_2$)$_4$]$_2$NCO, 30%), 121 (MeOPhCH$_2$, 100%).

$^1$H NMR (CDCl$_3$, 400 MHz, ppm): δ 0.85 (t, 6H), 1.1–1.3 (m, 8H), 1.44 (quintet, 4H), 2.58 (t, 2H), 2.67 (td, 1H), 2.73 (dd, 1H), 2.9–3.35 (m, 10H), 3.38–3.48 (m, 1H), 3.6–3.7 (3H), 3.79 (s, 3H), 3.83 (d, 1H), 4.44 (s, 1H), 5.14 (br d, 1H), 6.64–6.7 (m, 2H), 7.08 (app d, 4H), 7.12–7.35 (m, 8H), 7.40 (br t, 1H), 7.48 (br d, 1H).

EXAMPLE 16

(S)-4-(N,N-Di-n-pentylcarbamoyl)-1-(N,N-diphenylcarbamoyl)-2-(2-N-(benzyloxycarbonylmethyl)amino)ethylaminocarbonyl)piperazine Step A:
N-(t-Butoxycarbonyl)-N'-(benzyloxycarbonylmethyl)ethylenediamine A solution of 1.4 g (8.74 mmole) of N-(t-butoxycarbonyl)ethylenediamine (prepared in Example 2, Step A above), 1.35 mL (8.74 mmole) of benzyl 2-bromoacetate, and 1.53 mL (8.74 mmole) of DIEA in 18 mL of acetonitrile was stirred for 18 hr at room temperature. The mixture was then concentrated in vacuo and the residue purified by flash chromatography on 130 g of silica eluting with 2 L of 75:25 hexanes: ethyl acetate then 1 L of 100:4 methylene chloride:methanol to give 1.8 g (67%) of an oil.

$^1$H NMR (CDCl$_3$, 200 MHz, ppm): δ 1.40 (s, 9H), 2.72 (t, 2H), 3.17 (q, 2H), 3.41 (s, 2H), 4.95 (br s, 1H), 5.13 (s, 2H), 7.3–7.35 (m, 5H).]

Step B: N-(Benzyloxycarbonylmethyl)ethylenediamine bis(trifluoroacetic acid salt)

A mixture of 1.8 g (5,84 mmole) of N-(t-butoxycarbonyl)-N'-(benzyloxycarbonylmethyl)ethylenediamine and 4 mL of anisole at 0° C. was treated with 20 mL of ice cold trifluoroacetic acid. After two hr at 0° C., the mixture was concentrated in vacuo to give 2.67 g of a viscous oil.

$^1$H NMR (CD30D, 400 MHz, ppm): δ 3.3–3.4 (m, 2H), 3.4–3.45 (m, 2H), 4.12 (s, 2H), 5.28 (m, 2H), 7.3–7.45 (m 5H).

Step C:
(S)-4-(N,N-Di-n-pentylcarbamoyl)-1-(N,N-diphenylcarbamoyl)-2-(2-N-(benzyloxycarbonylmethyl)amino)ethylaminocarbonyl)piperazine A mixture of 100 mg (0.197 mmole) of (S)-1-(N,N-diphenylcarbamoyl)-4-(N,N-di-n-pentylcarbamoyl)piperazine-2-carboxylic acid and 32 mg (0.236 mmole) of HOBt in 6 mL of dry methylene chloride was cooled to 0° C. under an atmosphere of nitrogen. To this mixture was added 57 mg (0.295 mmole) of EDAC. The cooling bath was then removed and the solution was stirred for 40 min. The mixture was then treated with a solution of 172 mg (0.393 mmole) of N-(benzyloxycarbonylmethyl)ethylenediamine bis(trifluoroacetic acid salt) and 0.109 mL of triethylamine in 2 mL of methylene chloride and was stirred overnight. The mixture was purified by flash chromatography on 25 g of silica eluting with 500 mL of 100:4 methylene chloride: methanol, followed by flash chromatography on 23 g silica eluting with 100:3.5 methylene chloride:methanol, followed by flash chromatography on 23 g of silica with 300 mL of 100:2 methylene chloride:methanol, then 300 mL of 100:5 methylene chloride:methanol to give 61 mg (44%) of an oil, with a purity estimated at 90% by $^1$H NMR.

Mass Spectrum (FAB): m/Z 699 (M+H, 75%), 492 (10%), 306 (15%), 196 (80%), 184 (100%).

$^1$H NMR (CDCl$_3$, 400 MHz, ppm): δ 0.86 (t, 6H), 1.1–1.3 (8H), 1.46 (quintet, 4H), 2.68–2.8 (m, 4H), 3.0–3.4 (m, 7H), 3.4–3.5 (m, 3H), 3.71 (d, 1H), 3.95 (d, 1H), 4.28 (app d, 1H), 4.52 (s, 1H), 5.14 (s, 2H), 7.0–7.4 (15H).

EXAMPLE 17

(S)-4-(N,N-Di-n-pentylcarbamoyl)-1-(N,N-diphenylcarbamoyl)-2-(2-N-(benzyloxycarbonylmethyl)-N-methylamino)ethylaminocarbonyl)piperazine A solution of 0.041 mg (0.059 mmole) of (S)-4-(N,N-Di-n-pentylcarbamoyl)-1-(N,N-diphenylcarbamoyl)-2-(2-N-(benzyloxycarbonylmethyl)amino)ethyl aminocarbonyl)piperazine, 0.023 mL of aqueous formaldehyde and 6 mg (0.094 mmole) of sodium cyanoborohydride in 1.5 mL of acetonitrile was stirred for 15 min at room temperature. The pH was then adjusted to 6–6.5 with a solution of acetic acid/acetonitrile, and the mixture was stirred for one hr. Most of the volatiles were removed in a stream of nitrogen, and the residue was partitioned between 6 mL of ethyl acetate and 3 mL of saturated aqueous sodium bicarbonate. The aqueous layer was extracted with 3×4 mL of ethyl acetate, and the combined extracts were dried over sodium sulfate, filtered and concentrated in vacuo. The residue was purified by flash chromatography on 16 g of silica eluting with 400 mL of 25:74:0.5 hexanes:ethyl acetate:methanol to give 16 mg (38%) of an oil, which by $^1$H NMR contained 10-15% of an impurity.

Mass Spectrum (FAB): m/Z 714 (M+H, 95%), 492 (10%), 463 (9%), 306 (15%), 196 (Ph$_2$NCO, 85%), 184 ([CH$_3$(CH$_2$)$_4$]$_2$NCO, 100%).

$^1$H NMR (CDCl$_3$, 400 MHz, ppm): 6 0.85 (t, 6H), 1.1–1.3 (m, 8H), 1,45 (quintet, 4H), 2.38 (s, 3H), 2.6–2.7 (m, 3H), 2,84 (dd, 1H), 3.0–3.4 (m, 10H), 3.71 (d, 1H), 3.93 (d, 1H), 4.55 (s, 1H), 5.11 (s, 2H), 7.05–7.2 (m, 7H), 7.26–7.37 (m, 8H).

EXAMPLE 18

(RS)-1-(N,N-Diphenylcarbamoyl)-2-(2-(2-phenylethylamino)ethyl)-4-(N,N-dipentylcarbamoyl)piperazine

Step A: 2-(2-Hydroxyethyl)pyrazine

A mixture of 90.0 g (956 mmol) of 2-methylpyrazine and 6.4 g (212 mmol) of paraformaldehyde was heated in a stainless steel autoclave at 165° C. for 5 hours, The residue was distilled under iced aspirator pressure (ca. 10 mmHg) to yield 8.28 g (32%) of a light pink oil.

$^1$H NMR (400 MHz, CDCl$_3$) δ 3.02 (t, 2H), 4.02 (t, 2H), 8.37–8.50 (m, 3H).

Step B: (RS)-2-(2-Hydroxyethyl)piperazine

A solution of 1.80 g (14.50 mmol) of 2-(2-hydroxyethyl)pyrazine in 40 ml of methanol was hydrogenated over 24 hours using 0.8 g of platinum oxide, The reaction was filtered through Celite and TLC (10% methanol/0.2% ammonium hydroxide/chloroform) revealed that the reaction was 50% complete. The material was redissolved in 50 ml of methanol and hydrogenated again under the same conditions. The mixture was filtered through Celite and rinsed with 45 ml of methanol. Concentration in vacuo yielded 1.86 g (98%) of a yellow oil.

Step C: (RS)-2-(2-Trityloxyethyl)-4-N-tritylpiperazine

To a mixture of 255 mg (1.96 mmol) of (±) 2-(2-hydroxyethyl)piperazine and 1.25 g (4.50 mmol) of triphenylmethyl chloride in 5.0 ml of methylene chloride was added 550 ml (3.95 mmol) of triethylamine in one portion and the mixture was stirred at room temperature overnight under a nitrogen atmosphere. The reaction was diluted with 5 mL of methylene chloride and washed with water (3×5 ml) and the layers separated. The aqueous layer was extracted with 10 mL of methylene chloride. The organic layers were combined and washed with 15 mL of saturated sodium chloride solution, dried over anhydrous sodium sulfate, filtered, and concentrated in vacuo to an orange foam. Flash chromatography on 75 g of silica gel using a gradient elution of 1:9 v/v ethyl acetate/hexane to 1:9 v/v ethanol/ethyl acetate yielded 401 mg (33%) of a foam.

$^1$H-NMR (400 Fritz, CDCl$_3$) δ 1.49–1.67 (m, 2H), 2.84–3.22 (m, 7H), 3.35–3.48 (m, 2H), 7.02–7.43 (m, 30H).

Step D:
(RS)-1-(N,N-Diphenylcarbamoyl)-2-(2-trityloxyethyl)-4-N-tritylpiperazine To a suspension of 364 mg (0.59 mmol) of (±) 2-(2-trityloxyethyl)-4-N-tritylpiperazine in 10 ml of N,N-dimethylformamide was added 170 ml (1.22 mmol) of triethylamine in one portion and 140 mg (0.60 mmol) of diphenylcarbamyl chloride in portions and the mixture was allowed to stir under nitrogen at room temperature for 20 hours. The solution was cooled and concentrated in vacuo. Flash chromatography on 40 g of silica gel using 25:75 v/v ethyl acetate/hexane as the eluant afforded 240 mg (50%) of a yellow oil.

$^1$H-NMR (400 MHz, CDCl$_3$) δ 1.01–1.24 (m, 1H), 1.50–1.58 (br s, 1H), 2.17–2.52 (m, 3H), 2.74–2.86 (br d, 1H), 3.04–3.27 (m, 2H), 3.42–3.56 (m, 1H), 3.56–3.74 (br d, 1H), 4.02–4.20 (br s, 1H), 6.72–6.81 (d, 4H), 6.80–7.44 (m, 36H).

Step E:
(RS)-1-(N,N-Diphenylcarbamoyl)-2-(2-hydroxyethyl)piperazine

To a solution of 308 mg (0.38 mmol) of (±)-1-(N,N-diphenylcarbamoyl)-2-(2-trityloxyethyl)-4-N-tritylpiperazine in 30 mL of methanol was added 1.5 mL of trifluoroacetic acid and stirred at room temperature under nitrogen for 24 hours. The yellow solution was concentrated in vacuo. Flash chromatography on 60 g of silica gel using 95:5:0.5 methylene chloride:methanol::ammonium hydroxide as the eluant afforded 107 mg (86%) of a yellow oil.

$^1$H-NMR (400 MHz, CDCl$_3$) δ 1.74 (octet, 1H), 2.06 (br t, 1H), 2. 18 (br t, 1H), 2.52–2.58 (m, 3H), 2.78–3.02 (m, 3H), 3 .54–3.74 (m, 3H), 4.32–4.39 (m, 1H), 7.00–7.34 (m, 10H).

Mass Spectrum (FAB): m/z 326 (M+H, 100%), 243 (20%), 196 (70%).

Step F:
(RS)-1-(N,N-Diphenylcarbamoyl)-2-(2-hydroxyethyl)-4-(N,N-dipentylcarbamoyl)piperazine To a solution of 174 mg (0.53 mmol) of (RS)-1-(N,N-diphenylcarbamoyl)-2-(2-hydroxyethyl) piperazine in 10 mL of dry tetrahydrofuran was added 450ml (3.23 mmol) of triethylamine in one portion and 176 mg (0.80 mmol) of dipentylcarbamyl chloride (dissolved in 2 mL of dry tetrahydrofuran) and the mixture was stirred under nitrogen at 60° C. for two days. The solution was cooled and concentrated in vacuo. Flash chromatography on 25 g of silica gel using 75:25 v/v ethyl acetate/hexane as the eluant afforded 173 mg (64%) of a yellow oil.

$^1$H-NMR (400 MHz, CDCl$_3$) d 0.86 (t, 6H), 1.13–1.33 (m, 8H), 1 .44 (br quintet, 4H), 1.68–1.78 (m, 1H), 1.98–2 .07 (m, 1H), 2.07–2.17 (m, 1H), 2.95–3.15 (m, 7H), 3.38 (br d, 1H), 3.50–3.58 (m, 1H), 3.63–3.73 (m, 2H), 4.10–4.23 (br s, 1H), 4.35–4.42 (br d, 1H) 7.03 (d, 4H), 7.14 (t, 2H), 7.32 (t, 4H).

Mass Spectrum (FAB): m/z 510 (M+H, 60%), 341 (70%), 184 (100%).

Step G:
(RS)-1-(N,N-Diphenylcarbamoyl)-2-(2-bromoethyl)-4-(N,N-dipentylcarbamoyl)piperazine A solution of 312 mg (0.61 mmol) of (RS)-1-(N,N-diphenylcarbamoyl)-2-(2-hydroxyethyl)-4-(N,N-dipentylcarbamoyl)piperazine and 362 mL (0.86 mmol) of dibromotriphenylphosphorane in 15 mL of acetonitrile was stirred under nitrogen at 82° C. for 2 hours. The yellow solution was cooled and concentrated in vacuo. Flash chromatography on 35 g of silica gel using 1:1 v/v ethyl acetate/hexane as the eluant afforded 300 mg (85%) of a yellow oil.

$^1$H-NMR (400 MHz, CDCl$_3$) δ 0.86 (t, 6H), 1.13–1.33 (m, 9H), 1.44 (br quintet, 4H), 2.09 (sextet, 1H), 2.21 (sextet, 1H), 2.62–2.75 (m, 2H), 2.94–3.03 (m, 3H), 3.09–3.18 (m, 2H), 3.26 (br d, 1H), 3.33–3.43 (m, 3H), 3.77 (br d, 1H), 4.20–4.27 (br s, 1H), 7.05 (d, 4H), 7.24 (t, 2H), 7.29 (t, 4H).

Mass Spectrum(FAB): m/z 573 38%), 491 (75%), 402 ( 40%), 196 (100%).

Step H:

(RS)-1-(N,N-Diphenylcarbamoyl)-2-(2-(2-phenylethylamino)ethyl)-4-(N,N-dipentylcarbamoyl)piperazine A solution of 39.3 mg (0.069 mmol) of (RS)-1-(N,N-diphenylcarbamoyl)-2-(2-bromoethyl)-4-(N,N-dipentylcarbamoyl)piperazine in 1.0 ml of dry acetonitrile, 0.030 ml (0.24 mmol) of phenethylamine and 0.03 ml (0.17 mmol) of N,N-diisopropylethylamine was stirred at 82° C. for 3 hours. The solution was cooled and concentrated in vacuo. Flash chromatography on 15 g of silica gel using 95:5:0.5 methylene chloride:methanol:ammonium hydroxide as the eluant afforded 27.4 mg (65%) of a yellow oil.

$^1$H-NMR (400 MHz, CDCl$_3$) δ 0.85 (t, 6H), 1.01 (t, 6H), 1.1–1.3 (m, 8H), 1.44 (br quintet, 4H), 1.66–1.79 (m, 1H), 1.79–1.90 (m, 1H), 2.47–2.70 (m, 3H), 2.72–2.90 (m, 4H), 2.95–3.18 (m, 5H), 3.29 (m, 2H), 3.74 (br d, 1H), 4.18 (br s, 1H), 7.00 (d, 3H), 7.08–7.31 (m, 12H).

Mass Spectrum (FAB): m/z 612 (M+H, 100%), 565 (10%), 491 (20%), 417 (10%), 196 (30%).

EXAMPLE 19

(RS)-1-(N,N-Diphenylcarbamoyl)-2-(2-(benzylamino)ethyl)-4-(N,N-dipentylcarbamoyl)piperazine A solution of 30.5 mg (0.053 mmol) of (RS)-1-(N,N-diphenylcarbamoyl)-2-(2-bromoethyl)-4-(N,N-Dipentylcarbamoyl)piperazine in 1.0 ml of dry acetonitrile, 0.035 ml (0.32 mmol) of benzylamino and 0.019 ml (0.11 mmol) of N,N-diisopropylethylamine was stirred at 82° C. for 2 hours. The solution was cooled and concentrated in vacuo. Flash chromatography on 15 g of silica gel using 95:5:0.5 methylene chloride:methanol:ammonium hydroxide as the eluant afforded 23.1 mg (72%) of a yellow oil.

$^1$H-NMR (400 MHz, CDCl$_3$) δ 0.85 (t, 6H), 1.14–1.20 (m, 4H), 1 .25 (br quintet , 4H), 1.42 (br quintet, 4H), 1.75–1.92 (m, 2H), 2 .45–2.55 (m, 1H), 2.55–2.70 (m, 2H), 2 .81 (br d, 1H), 2.98 (quintet, 2H), 3.05–3.15 (m, 3H), 3.30 ( app t, 2H), 3.75 (s, 3H), 4.20–4.28 (m, 1H), 7.00 ( d, 3H), 7.12 (t, 2H), 7.20–7.30 (m, 9H).

Mass Spectrum (FAB): m/z 598 (M+H, 100%), 491 (38%), 404 (20%).

EXAMPLE 20

(RS)-1-(N,N-Diphenylcarbamoyl)-2-(2-(3-phenylpropylamino)ethyl)-4-(N,N-dipentylcarbamoyl)piperazine A solution of 41.2 mg (0.072 mmol) of (RS)-1-(N,N-diphenylcarbamoyl)-2-(2-bromoethyl)-4-(N,N-dipentylcarbamoyl)piperazine in 1.0 ml of dry acetonitrile, 0.061 ml (0.43 mmol) of 3-phenylpropylamine and 0.025 ml (0.14 mmol) of N,N-diisopropylethylamine was stirred at 60° C. for 2 hours. The solution was cooled and concentrated in vacuo. Flash chromatography on 18 g of silica gel using 95:5:0.5 methylene chloride:methanol:ammonium hydroxide as the eluant afforded 24.6 mg (55%) of a yellow oil.

$^1$H-NMR (400 MHz, CDCl$_3$) δ 0.85 (t, 6H), 1.12–1.21 (m, 4H), 1.21–1.31 (m, 4H), 1.44 (br quintet, 4H), 1.79 (br quintet, 3H), 1.87–2.00 (m, 1H), 2.41–2.50 (m, 1H), 2.56–2.70 (m, 6H), 2.83 (br d, 1H), 3.00 (quintet, 3H), 3.06–3.16 (m, 3H), 3.26–3.35 (m, 2H), 3.72 (br d, 1H), 4.18–4.26 (m, 1H), 7.01 (d, 4H), 7.08–7.18 (m, 6H), 7.21–7.30 (m, 6 H).

Mass Spectrum (FAB): m/z 627 (M+H, 100%), 196 (19%), 168 (19%).

EXAMPLE 21

(RS)-1-(N,N-Diphenylcarbamoyl)-2-(2-(2-(2-methoxyphenyl)ethylamino)ethyl)-4-(N,N-dipentylcarbamoyl)piperazine A solution of 39.2 mg (0.069 mmol) of (RS)-1-(N,N-diphenylcarbamoyl)-2-(2-bromoethyl)-4-(N,N-dipentylcarbamoyl)piperazine in 1.0 ml of dry acetonitrile, 0.060 ml (0.41 mmol) of 2-methoxyphenethylamine and 0.024 ml (0.14 mmol) of N,N-diisopropylethylamine was stirred at 80° C. for 1 hour. The solution was cooled and concentrated in vacuo. Flash chromatography on 19 g of silica gel using 95:5:0.5 methylene chloride:methanol:ammonium hydroxide as the eluant afforded 24.3 mg (55%) of a yellow oil.

$^1$H-NMR (400 MHz, CDCl$_3$) δ 0.85 (t, 6H), 1.12–1.22 (m, 4H ), 1.27 (br quintet, 4H), 1.44 (br quintet, 4H), 1 .72–1.96 (m, 2H), 2.45–2.55 (m, 1H), 2.61–2.70 (m, 2H ), 2.76–2.87 (m, 5H), 2.94–3.05 (quintet, 3H), 3.05–3 .16 (m, 3H), 3.25–3.34 (m, 2H), 3.7 2 (br s, 1H), 3.75 (s, 3H), 4.16–4.23 (m, 1H), 6.8 2 (q, 2H), 7.00 (d, 4H), 7.06–7.19 (m, 4H), 7.25–7.3 0 (m, 4H).

Mass Spectrum (FAB): m/z 643 (M+H, 100%) , 491 (30%), 447 (38%).

EXAMPLE 22

(RS)-1-(N,N-Diphenylcarbamoyl)-2-(2-(2-(3,5-dimethylphenyl)ethylamino)ethyl)-4-(N,N-dipentylcarbamoyl)piperazine A solution of 38.6 mg (0.068 mmol) of (RS)-1-N,N-Diphenylcarbamoyl)-2-(2-bromoethyl)-4-(N,N-dipentylcarbamoyl)piperazine in 1.0 ml of dry acetonitrile, 60 mg (0.41 mmol) of 2-(3,5-dimethylphenyl)ethylamine and 0.024 ml (0.14 mmol) of N,N-diisopropylethylamine was stirred at 60° C. for 2 hours. The solution was cooled and concentrated in vacuo. Flash chromatography on 18 g of silica gel using 95:5:0.5 methylene chloride:methanol:ammonium hydroxide as the eluant afforded 24.9 mg (58%) of a yellow oil.

$^1$H-NMR (400 MHz, CDCl$_3$) δ 0.85 (t, 6H), 1.14–1.32 (m, 9H), 1.44 (br quintet, 5H) 1.70–1.91 (m, 2H), 2.25 (s, 6H), 2.50–2.71 (m, 4H 2.76–2.84 (m, 3H), 2.95–3.16 (m, 6H), 3.30 (app t , 2H), 3.75 (br d, 1H), 4.16–4.23 (m, 1H), 6.77 (s, 2H ), 6.81 (s, 1H), 7.00 (d, 4H), 7.12 (t, 2H), 7.29 (t , 4H).

Mass Spectrum (FAB): m/z 641 (M+H, 100%), 492 (19%), 296 (28%), 196 (42%), 168 (35% ), 133 (58%).

EXAMPLE 23

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| Active ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the active ingredient (25 mg), pregelatinized starch USP (82 mg), microcrystalline cellulose (82 mg) and magnesium stearate (1 mg).

C: Suppository

Typical suppository formulations for rectal administration contain the active ingredient (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

D: Injection

A typical injectible formulation contains the acting ingredient sodium phosphate dibasic anhydrous (11.4 mg), benzyl alcohol (0.01 ml) and water for injection (1.0 ml).

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound which is selected from the group consisting of:

1) 4-(N,N-di-n-pentylcarbamoyl)-1-(N,N -diphenyl-carbamoyl)-N-[3-(4-morpholinyl)propyl]-2-piperazinecarboxamide;

2) 4-(N,N-di-n-pentylcarbamoyl)-1-(N,N-diphenyl-carbamoyl)-N-[2-(4-morpholinyl)ethyl]-2-piperazinecarboxamide;

3) 4-(N,N-di-n-pentylcarbamoyl)-1-(N,N-diphenyl-carbamoyl)-N-[2-(1-piperidinyl)ethyl]-2-piperazinecarboxamide;

4) 4-(N,N-di-n-pentylcarbamoyl)-1-(N,N-diphenyl-carbamoyl)-N-[2-(acetamido)ethyl]-2-piperazinecarboxamide;

5) 4-(N,N-di-n-pentylcarbamoyl)-1-(N,N-diphenyl-carbamoyl)-N-[2-(N'-benzyl-N'-methylamino)-ethyl]-N-methyl-2-piperazinecarboxamide;

6) 4-(N,N-di-n-pentylcarbamoyl)-1-(N,N-diphenyl-carbamoyl)-N-[3-(benzyloxycarbonyl)propyl]-N-methyl-2-piperazinecarboxamide;

7) 4-(N,N-di-n-pentylcarbamoyl)-1-(N,N-diphenyl-carbamoyl)-N-[2-[(N'-(3,5-dimethylphenyl)-methyl-(N'-methyl)amino]ethyl]-N-methyl-2-piperazinecarboxamide;

8) 4-(N,N-di-n-pentylcarbamoyl)-1-(N,N-diphenyl-carbamoyl)-N-[2-[(N'-[3,5-di-(trifluoro-methyl)phenyl]-methyl)-(N'-methyl)amino]ethyl]-N-methyl-2-piperazinecarboxamide;

9) 4-(N,N-di-n-pentylcarbamoyl)-1-(N,N-diphenyl-carbamoyl)-N-[2-[(N'-(2-methoxyphenyl)-methyl)-(N'-methyl) amino]ethyl]-N-methyl-2-piperazinecarboxamide;

10) 4-(N,N-di-n-pentylcarbamoyl)-1-(N,N-diphenyl-carbamoyl)-N-[2-(N'-[(1,1-dimethyl)ethoxy-carbonyl]-(N'-methyl)aminoethyl]-N-methyl-2-piperazinecarboxamide;

11) (S)-2-(2-(N-(2-methoxybenzyl)amino)ethylaminocarbonyl)-4-(N,N-di-n-pentylcarbamoyl)-1-(N,N-diphenylcarbamoyl)-piperazine;

12) 2-(2-(N-methyl-N-(2-methoxybenzyl)amino)-ethylamino-carbonyl)-4-(N,N-di-n-pentylcarbamoyl)-1-(N,N-diphenylcarbamoyl)piperazine;

13) (S)-2-(2-(1-piperidinyl)ethylaminocarbonyl)-1-[N-(3-chlorophenyl)-N-phenylcarbamoyl]-4-(N,N-di-n-pentylcarbamoyl)piperazine;

14) (S)-2-(2-(1-piperidinyl)ethylaminocarbonyl)-4-(N,N-di-n-pentylcarbamoyl)-1-(N,N-diphenyl-carbamoyl)piperazine;

15) (S)-2-(2-(N,N-bis(2-methoxybenzyl)amino)-ethylamino-carbonyl)-1-(N,N-diphenylcarbamoyl)-4-(N,N-di-n-pentylcarbamoyl)piperazine;

16) (S)-4-(N,N-di-n-pentylcarbamoyl)-1-(N,N-diphenyl-carbamoyl)-2-(2-(4-morpholinyl)ethylaminocarbonyl)-piperazine;

17) (S)-2-(2-(N-benzyl-N-methylamino)-N-(methyl)ethylaminocarbonyl)-4-(N,N-di-n-pentylcarbamoyl)-1-(N,N-diphenylcarbamoyl)piperazine;

18) (S)-1-(N-(3-chlorophenyl)-N-phenylcarbamoyl)-2-(2-(N-methyl-N(2-methoxybenzyl)amino)-ethylaminocarbonyl)-4-(N,N-di-n-pentylcarbamoyl)-piperazine;

19) (S)-1-(N-(3,5-dimethylphenyl)-N-phenylcarbamoyl)-2-(2-(N-methyl-N-(2-methoxybenzyl)-amino)ethylaminocarbonyl)-4-(N,N-di-n-pentyl-carbamoyl)-piperazine;

20) (S)-1-(N-(3,5-dichlorophenyl)-N-phenylcarbamoyl)-2-(2-(N-methyl-N-(2-methoxybenzyl)-amino)ethylaminocarbonyl)-4-(N,N-di-n-pentyl-carbamoyl)piperazine;

21) (S)-4-(N,N-di-n-pentylcarbamoyl)-1-(N,N-diphenyl-carbamoyl)-2-(2-N-(benzyloxycarbonylmethyl)amino)-ethylaminocarbonyl)piperazine;

22) (S)-4-(N,N-di-n-pentylcarbamoyl)-1-(N,N-diphenyl-carbamoyl)-2-(2-N-(benzyloxycarbonylmethyl)-N-methylamino)ethylaminocarbonyl)piperazine;

or a pharmaceutically acceptable salt thereof.

2. A compound which is selected from the group consisting of:

1) 2-[2-((N-[2-(N'-benzyl -N'-methyl)aminoethyl])-N -methyl)aminoethyl]-4-(N,N-di-n-pentyl-carbamoyl)-1-(N,N-diphenylcarbamoyl)-piperazine;

2) 2-[2-(N,N-dibenzylamino)ethyl]-4-(N,N-di-n-pentyl-carbamoyl)-1-(N,N-diphenylcarbamoyl)-piperazine;

3) 2-[2-(N -[2-phenylethyl]amino)ethyl]-4-(N,N -di-n-pentylcarbamoyl)-1-(N,N-diphenyl-carbamoyl)piperazine;

4) 2-[2-(N-benzylamino)ethyl]-4-(N,N-di-n-pentylcarbamoyl)-1-(N,N-diphenylcarbamoyl)-piperazine;

5) 2-[2-(N -[4-phenylbutyl]amino)ethyl]-4-(N,N-di-n-pentylcarbamoyl)-1-(N,N-diphenyl-carbamoyl)piperazine;

6) 4-(N,N-di-n-pentylcarbamoyl)-1-(N,N-diphenyl-carbamoyl)-2-(2-(3-phenylpropylamino)ethyl)-piperazine;

7) 4-(N,N-di-n-pentylcarbamoyl)-1-(N,N-diphenyl-carbamoyl)-2-(2-(2-(2-methoxyphenyl)ethylamino)ethyl)piperazine;

8) 2-(2-(2-(3,5-di-methylphenyl)ethylamino)ethyl)-4-(N,N -di-n-pentylcarbamoyl)-1-(N,N-di-phenylcarbamoyl)piperazine;

or a pharmaceutically acceptable salt thereof.

3. A pharmaceutical composition comprising a pharmaceutically acceptable carrier and an effective amount of the compound of claim 1.

4. A pharmaceutical composition comprising a pharmaceutically acceptable carrier and an effective amount of the compound of claim 2.

* * * * *